United States Patent [19]
Kunkel et al.

[11] Patent Number: 5,541,074
[45] Date of Patent: Jul. 30, 1996

[54] ANTIBODIES TO DYSTROPHIN AND USES THEREFOR

[75] Inventors: Louis M. Kunkel, Hyde Park; Anthony Monaco, Boston; Eric P. Hoffman, Newton; Michel Koenig, Boston, all of Mass.

[73] Assignee: The Children's Medical Center Corporation, Boston, Mass.

[21] Appl. No.: 342,793

[22] Filed: Nov. 21, 1994

Related U.S. Application Data

[63] Continuation of Ser. No. 971,057, Nov. 3, 1992, abandoned, which is a continuation of Ser. No. 136,618, Dec. 22, 1987, Pat. No. 5,239,060, which is a continuation-in-part of Ser. No. 890,694, Jul. 25, 1986, abandoned.

[51] Int. Cl.$^6$ .................. G01N 33/567; C07K 16/18
[52] U.S. Cl. .................. 435/7.21; 530/387.1; 530/388.2; 530/389.1; 435/7.1; 435/7.2; 435/7.95; 436/63; 436/518; 436/811; 514/907
[58] Field of Search .................. 530/387.1, 388.2, 530/389.1, 839, 841; 435/7.21, 7.1, 7.92, 7.95; 436/519, 518, 547, 63; 514/907

[56] References Cited

U.S. PATENT DOCUMENTS

| | | | |
|---|---|---|---|
| 5,187,063 | 2/1993 | Campbell et al. | 435/7.21 |
| 5,260,209 | 11/1993 | Campbell et al. | 435/240.2 |
| 5,308,752 | 5/1994 | Campbell et al. | 435/7.21 |
| 5,340,718 | 8/1994 | Ishiguro et al. | 435/7.1 |
| 5,413,910 | 5/1995 | Campbell et al. | 435/7.21 |
| 5,430,129 | 7/1995 | Campbell et al. | 530/395 |

OTHER PUBLICATIONS

Roitt (1991) "Essential Immunology", Blackwell Scientific Publications, Oxford, pp. 65–68 & 74.
Monaco et al. (1986) (16 Oct.) Nature 323:646–650.
Hoffman et al (1989) J. Cell Biol. 108:503–510.
Lehninger (1970) "Biochemistry", Worth Publishers, Inc., New York. pp. 713–726.
Koenig et al (1987) Cell 50:509–517.
Hoffman et al (1987) Cell 51:919–928.
Walter (1986) J. Immunol. Methods. 88:149–161.
Goding (1983) "Monoclonal Antibodies: Principles and Practice", Academic Press, Inc., Orlando, pp. 56–91 and 134–181.
Swiss–Prot. 24 Database, Searched Using Intelligenetics Software. Sequence (amino acid) Search of Human Dystrophin; Performed May 6, 1993 (3 pages).
Matsumura et al (1989) Biomedical Research 10:325–328.
Hammonds Jr., G. R., "Protein Sequence of DMD Gene Is Related to Actin–Binding Domain of α–Actinin", *Cell*. 51(1) (1987).
Smith, T. J., et al., "Isolation of a conserved sequence deleted in Duchenne muscular dystrophy patients", *Nucleic Acids Research* 15(5):2166–2173 (1987).
Koga, K., et al., "Western Blotting Method For Detecting Antibodies Against Human Muscle Contractile Proteins In Myositis", *J. Immunol. Methods*, 105(1):15–22 (1987).

Cross, G. S., et al., "Deletions Of Fetal And Adult Muscle Complementary DNA In Duchenne And Becker Muscular Dystrophy Patients", *EMBO Journal (Eur. Mol. Biol. Organ.)*, 6(11):3277–3284 (1987).
Hart, K. A., et al., "A Small Deletion In The Duchenne–Becker Muscular Dystrophy Locus A Functionally Important Region?", *Hum. Genet.*, 77(1):88–91 (1987).
Davies et al., Nucleic Acid Research 13(1):155–165 (1985).
Kunkel et al., Gene 33:251–258 (1985).
Ray et al., Nature 318:672 (1985).
Monaco et al., Nature 316:842 (1985).
Kunkel et al., Proc. Nat. Acad. Sci. 82:4788 (1985).
Bakker et al., The Lancet I:655 (1985).
Francke et al., Am. J. Hum. Genet. 37:250 (1985).
Martinville et al., Am. J. Hum. Genet. 37:235 (1985).
Aldridge et al., Am. J. Hum. Genet. 36:546 (1984).
Davies et al., Nuc. Acid. Res. 11:2303 (1983).
Fryns et al., Clin. Genet. 22:76 (1982).
Mohandas et al., Proc. Nat. Acad. Sci. 77:6759 (1980).
Greenstein et al., Cytogenet. Cell. Genet. 27:268 (1980).
G. J. B. van Ommen et al., Cell 47:499–504 (1986).
J. Koch et al., Nucleic Acid Research 1(17):7133 (1986).
Speer et al., 3–Biochem. Genetics 105:149 (1986).
Kolata, Research News 669–670 (1986).
Hoffman et al., Science 238:347–350 (1987).
Heiliq et al., Nature 328:168–170 (1987).
Brockdorff et al., Nature 328:166–168 (1987).
Burghes et al., Nature 328:434–437 (1987).
Lev et al., J. Biol. Chem. 262:15817–820 (1987).
Lancet, "Dystrophin" 2(8608):429–30 (1988).
Hoffman et al., Nature 330:754–758 (1987).
Mandel, Nature 339:584–586 (1989).
Bowie et al., Science 247:1306–1310 (1990).

*Primary Examiner*—Margaret Parr
*Assistant Examiner*—Jacqueline G. Krikorian
*Attorney, Agent, or Firm*—Hamilton, Brook, Smith & Reynolds, P.C.

[57] ABSTRACT

The invention relates to a muscular dystrophy (MD) probe comprising a substantially purified single-stranded nucleic acid sequence capable of hybridizing to a region of DNA on a human X chromosome between the deletion break point at Xp21.3 and the translocation break point at X;11. The invention also relates to a 14 kb cDNA corresponding to the complete MD gene and probes produced therefrom useful in genetic methods of diagnosis of MD. Furthermore, the invention relates to the polypeptide, dystrophin, which corresponds to the MD gene product, and antibodies thereto that are useful in a variety of methods for immunodiagnosis of MD.

9 Claims, 25 Drawing Sheets

```
TTCTGTCTTAGTGAAGTCTCAAT-ATTTTTCAATGTGATTAAAATTCATATTATGTCACC
ATAGTTATGAAAAAAGTAAAAATATGTTTTGTATAAGTCTTAT-ATTTGATAATTTAAGC
CAATTAACAAATCCTGACAGCTGGTGTAGAATTTGAGATAAAATTCCCCTGCTGACTCAG
GCAGTGAATAAGAATTTAATGTTCATTAAAATATGTCATAATCTGAGACCCAAAGCAGGT
ACCATCTGTTTCCAGTTCCTACTACATGCCTAGGTATGGAATCCATGTTCTAAAATTCTT
TTTAATTTACAACAAGTATAATTTATTTCGAAATAGCATCATCAATAACCAGTGTAATTC
TCGAATATTTTGTTGGGATTGTTATCTGAGAAATGTGGTATTTCATTTCTTTACAA
----------------------------------------------------------
GCAAGTCATGAAATGGCTCATGCTTTTATTGCCATTTTGATGTTTTGATGGCAAAAGTG
TTGAGAAA-AAGTCTT-TAGATTCACGTGATAAGCTGACAGAGTGAAACATCTTAAGGCT
TGAAAGGGCAAGTAGAAGTTATAATTATTGTGTAGATTCACAGTCCTTGTATTGAATTAG
TCATCTTTGCTCTCATGCTGCAGGCCATAGAGCGAGAAAAAGCTGAGAAGTTCAGAAAAC
TGCAAGATGCCAGCAGATCAGCTCAGGCCCTGGTGGAACAGATGGTGAATGGTAATTACA
CG-AGTTGATTTAGATAATCTTCTTAGGGATTTGATAAACACATAGGTTCATATTTATCA
GCTGAATTATATCAGACAAGCACTTGTTAAATACAAATTTAAATTAAAAGGTGTTTGTAT
GTTTTTATTATTCTTTTTTTAATGCTAAGGAAATTATTAGGAGAAATTCAACTTTGAGT
TCATTGGAAGAAAATGGGATGTGGTAGAATATTTTATCAGTCTGTAGCAGAGAAATAAAT
TTTAATGCAAATCTG-CT-AGAATTTATCCAAATAATTTAAGAAATAAGGT-TAACAGAA
ATTGAAACATTAACAGTCAAGTATA
```

FIG. 3

```
GGGATTCCCTCACTTTCCCCCTACAGGACTCAGATCTGGGAGGCAATTACCTTCGGAGAA
AAACGAATAGGAAAAACTGAAGTGTTACTTTTTTAAAGCTGCTGAAGTTTGTTGGTTTC
TCATTGTTTTAAGCCTACTGGAGCAATAAAGTTTGAAGAACTTTTACCAGGTTTTTTTT
ATCGCTGCCTTGATATACACTTTTCAAAATGCTTTGGTGGGAAGAAGTAGAGGACTGTTA
TGAAAGAGAAGATGTTCAAAGAAAACATTCACAAATGGGTAAATGCACAATTTTCTAA
GTTTGGGAAGCAGCATATTGAGAACCTCTTCAGTGACCTACAGGATGGGAGGCGCCTCCT
AGACCTCCTCGAAGGCCTGACAGGGCAAAAACTGCCAAAAGAAAAGGATCCACAAGAGT
TCATGCCCTGAACAATGTCAACAAGGCACTGCGGGTTTTGCAGAACAATAATGTTGATTT
AGTGAATATTGGAAGTACTGACATCGTAGATGGAAATCATAAACTGACTCTTGGTTTGAT
TTGGAATATAATCCTCCACTGGCAGGTCAAAATGTAATGAAAATATCATGGCTGGATT
GCAACAAACCAACAGTGAAAGATTCTCCTGAGCTGGGTCCGACAATCAACTCGTAATTA
TCCACAGGTTAATGTAATCAACTTCACCACCAGCTGGTCTGATGGCCTGGCTTTGAATGC
TCTCATCCATAGTCATAGGCCAGACCTATTTGACTGGAATAGTGTCCTTTGCCAGCAGTC
AGCCACACAACGACTGGAACATGCATTCAACATCGCCAGATATCAATTAGGCATAGAGAA
ACTACTCGATCCTGAAGATGTTGATACCACCTATCCAGATAAGAAGTCCATCTTAATGTA
CATCACATCACTCTTCCAAGTTTTGCCTCAACAAGTGAGCATTGAAGCCATCCAGGAAGT
GGAAATGTTGCCAAGGCCACCTAAAGTGACTAAAGAAGAACATTTTCAGTTACATCATCA
AATGCACTATTCTCAACAGATCACGGTCAGTCTAGCACAGGGATATGAGAGAACTTCTTC
CCCTAAGCCTCGATTCAAGAGCTATGCCTACACACAGGCTGCTTATGTCACCACCTCTGA
CCCTACACGGAGCCCATTTCCTTCACAGCATTTGGAAGCTCCTGAAGACAAGTCATTTGG
CAGTTCATTGATGGAGAGTGAAGTAAACCTGGACCGTTATCAAACAGCTTTAGAAGAAGT
ATTATCGTGGCTTCTTTCTGCTGAGGACACATTGCAAGCACAAGGAGAGATTTCTAATGA
TGTGGAAGTGGTGAAAGACCAGTTTCATACTCATGAGGGGTACATGATGGATTTGACAGC
CCATCAGGGCCGGGTTGGTAATATTCTACAATTGGGAAGTAAGCTGATTGGAACAGGAAA
ATTATCAGAAGATGAAGAAACTGAAGTACAAGAGCAGATGAATCTCCTAAATTCAAGATG
GGAATGCCTCAGGGTAGCTAGCATGGAAAAACAAAGCAATTTACATAGAGTTTTAATGGA
TCTCCAGAATCAGAAACTGAAAGAGTTAATGACTGGCTAACAAAACAGAAGAAAGAAC
AAGGAAAATGGAGGAAGAGCCTCTTGGACCTGATCTTGAAGACCTAAAACGCCAAGTACA
ACAACATAAGGTGCTTCAAGAAGATCTAGAACAAGAACAAGTCAGGGTCAATTCTCTCAC
TCACATGGTGGTGGTAGTTGATGAATCTAGTGGAGATCACGCAACTGCTGCTTTGGAAGA
ACAACTTAAGGTATTGGGAGATCGATGGGCAAACATCTGTAGATGGACAGAAGACCGCTG
GGTTCTTTTACAAGACATCCTTCTCAAATGGCAACGTCTTACTGAAGAACAGTGCCTTTT
TAGTGCATGGCTTTCAGAAAAAGAAGATGCAGTGAACAAGATTCACACAACTGGCTTTAA
AGATCAAAATGAAATGTTATCAAGTCTTCAAAAACTGGCCGTTTTAAAAGCGGATCTAGA
AAAGAAAAAGCAATCCATGGGCAAACTGTATTCACTCAAACAAGATCTTCTTTCAACACT
GAAGAATAAGTCAGTGACCCAGAAGACGGAAGCATGGCTGGATAACTTTGCCCGGTGTTG
GGATAATTTAGTCCAAAAACTTGAAAAGAGTACAGCACAGATTTCACAGGCTGTCACCAC
CACTCAGCCATCACTAACACAGACAACTGTAATGGAAACAGTAACTACGGTGACCACAAG
GGAACAGATCCTGGTAAAGCATGCTCAAGAGGAACTTCCACCACCACCTCCCCAAAAGAA
GAGGCAGATTACTGTGGATTCTGAATTAGGAAAAGGTTGGATGTTGATATAACTGAACT
TCACAGCTGGATTACTCGCTCAGAAGCTGTGTTGCAGAGTCCTGAATTTGCAATCTTTCG
GAAGGAAGGCAACTTCTCAGACTTAAAAGAAAAGTCAATGCCATAGAGCGAGAAAAAGC
TGAGAAGTTCAGAAAACTGCAAGATGCCAGCAGATCAGCTCAGGCCCTGGTGGAACAGAT
GGTGAATGAGGGTGTTAATGCAGATAGCATCAAACAAGCCTCAGAACAACTGAACAGCCG
GTGGATCGAATTCTGCCAGTTGCTAAGTGAGAGACTTAACTGGCTGGAGTATCAGAACAA
CATCATCGCTTTCTATAATCAGCTACAACAATTGGAGCAGATGACAACTACTGCTGAAAA
CTGGTTGAAAATCCAACCCACCACCCCATCAGAGCCAACAGCAATTAAAAGTCAGTTAAA
AATTTGTAAGGATGAAGTCAACCGGCTATCAGGTCTTCAACCTCAAATTGAACGATTAAA
AATTCAAAGCATAGCCCTGAAAGAGAAAGGACAAGGACCCATGTTCCTGGATGCAGACTT
```

FIG. 5A

```
TGTGGCCTTTACAAATCATTTTAAGCAAGTCTTTTCTGATGTGCAGGCCAGAGAGAAAGA
GCTAGAGACAATTTTTGACACTTTGCCACCAATGCGCTATCAGGAGACCATGAGTGCCAT
CAGGACATGGGTCCAGCAGTCAGAAACCAAACTCTCCATACCTCAACTTAGTGTCACCGA
CTATGAAATCATGGAGCAGAGACTCGGGGAATTGCAGGCTTTACAAAGTTCTCTGCAAGA
GCAACAAAGTGGCCTATACTATCTCAGCACCACTTTGAAAGAGATGTCGAAGAAAGCGCC
CTCTGAAATTAGCCGGAAATATCAATCAGAATTTGAAGAAATTGAGGGACGCTGGAAGAA
GCTCTCCTCCCAGCTGGTTGAGCATTGTCAAAGCTAGAGGAGCAAATGAATAAAGTCCG
AAAAATTCAGAATCACATACAAACCCTGAAGAAATGGATGGCTGAAGTTGATGTTTTTCT
GAAGGAGGAATGGCCTGCCCTTGGGGATTCAGAAATTCTAAAAAGCAGCTGAAACAGTG
CAGACTTTTAGTCAGTGATATTCAGACAATTCAGCCCAGTCTAAACAGTGTCAATGAAGG
TGGGCAGAAGATAAAGAATGAAGCAGAGCCAGAGTTTGCTTCGAGACTTGAGACAGAACT
CAAAGAACTTAACACTCAGTGGGATCACATGTGCCAACAGGTCTATGCCAGAAAGGAGGC
CTTGAAGGGAGGTTTGGAGAAAACTGTAAGCCTCCAGAAAGATCTATCAGAGATGCACGA
ATGGATGACACAAGCTGAAGAAGAGTATCTTGAGAGAGATTTTGAATATAAAACTCCAGA
TGAATTACAGAAAGCAGTTGAAGAGATGAAGAGAGCTAAAGAAGAGGCCCAACAAAAGA
AGCGAAAGTGAAACTCCTTACTGAGTCTGTAAATAGTGTCATAGCTCAAGCTCCACCTGT
AGCACAAGAGGGCTTAAAAAAGGAACTTGAAACTCTAACCACCAACTACCAGTGGCTCTG
CACTAGGCTGAATGGGAAATGCAAGACTTTGGAAGAAGTTTGGGCATGTTGGCATGAGTT
ATTGTCATACTTGGAGAAAGCAAACAAGTGGCTAAATGAAGTAGAATTTAAACTTAAAAC
CACTGAAAACATTCCTGGCGGAGCTGAGGAAATCTCTGAGGTGCTAGATTCACTTGAAAA
TTTGATGCGACATTCAGAGGATAACCCAAATCAGATTCGCATATTGGCACAGACCCTAAC
AGATGGCGGAGTCATGGATGAGCTAATCAATGAGGAACTTGAGACATTTAATTCTCGTTG
GAGGGAACTACATGAAGAGGCTGTAAGGAGGCAAAAGTTGCTTAACAGAGCATCCAGTC
TGCCCAGGAGACTGAAAAATCCTTACACTTAATCCAGGAGTCCCTCACATTCATTGACAA
GCAGTTGGCAGCTTATATTGCAGACAAGGTGGACGCAGCTCAAATGCCTCAGGAAGCCCA
GAAAATCCAATCTGATTTGACAAGTCATGAGATCAGTTTAGAAGAAATGAAGAAACATAA
TCAGGGGAAGGAGGCTGCCCAAAGAGTCCTGTCTCAGATTGATGTTGCACAGAAAAAATT
ACAAGATGTCTCCATGAAGTTTCGATTATTCCAGAAACCAGCCAATTTTGAGCTGCGTCT
ACAAGAAAGTAAGATGATTTTAGATGAAGTGAAGATGCACTTGCCTGCATTGGAAACAAA
GAGTGTGGAACAGGAAGTAGTACAGTCACAGCTAAATCATTGTGTGAACTTGTATAAAAG
TCTGAGTGAAGTGAAGTCTGAAGTGGAAATGGTGATAAAGACTGGACGTCAGATTGTACA
GAAAAAGCAGACGGAAAATCCCAAAGAACTTGATGAAAGAGTAACAGCTTTGAAATTGCA
TTATAATGAGCTGGGAGCAAAGGTAACAGAAACAAAGCAACAGTTGGAGAAATGCTTGAA
ATTGTCCCGTAAGATGCGAAAGGAAATGAATGTCTTGACAGAATGGCTGGCAGCTACAGA
TATGGAATTGACAAAGAGATCAGCAGTTGAAGGAATGCCTAGTAATTTGGATTCTGAAGT
TGCCTGGGGAAAGGCTACTCAAAAAGAGATTGAGAAACAGAAGGTGCACCTGAAGAGTAT
CACAGAGGTAGGAGAGGCCTTGAAAACAGTTTTGGGCAAGAAGGAGACGTTGGTGGAAGA
TAAACTCAGTCTTCTGAATAGTAACTGGATAGCTGTCACCTCCCGAGCAGAAGAGTGGTT
AAATCTTTTGTTGGAATACCAGAAACACATGGAAACTTTTGACCAGAATGTGGACCACAT
CACAAAGTGGATCATTCAGGCTGACACACTTTTGGATGAATCAGAGAAAAGAAACCCCA
GCAAAAAGAAGACGTGCTTAAGCGTTTAAAGGCAGAACTGAATGACATACGCCCAAGGT
GGACTCTACACGTGACCAAGCAGCAAACTTGATGGCAAACCGCGGTGACCACTGCAGGAA
ATTAGTAGAGCCCCAAATCTCAGAGCTCAACCATCGATTTGCAGCCATTTCACACAGAAT
TAAGACTGGAAAGGCCTCCATTCCTTTGAAGGAATTGGAGCAGTTTAACTCAGATATACA
AAAATTGCTTGAACCACTGGAGGCTGAAATTCAGCAGGGGTGAATCTGAAAGAGGAAGA
CTTCAATAAAGATATGAATGAAGACAATGAGGGTACTGTAAAAGAATTGTTGCAAAGAGG
AGACAACTTACAACAAAGAATCACAGATGAGAGAAGAGAGAGGAAATAAAGATAAAACA
GCAGCTGTTACAGACAAAACATAATGCTCTCAAGGATTTGAGGTCTCAAAGAAGAAAAAA
GGCTCTAGAAATTTCTCATCAGTGGTATCAGTACAAGAGGCAGGCTGATGATCTCCTGAA
```

FIG. 5B

```
ATGCTTGGATGACATTGAAAAAAAATTAGCCAGCCTACCTGAGCCCAGAGATGAAAGGAA
AATAAAGGAAATTGATCGGGAATTGCAGAAGAAGAAAGAGGAGCTGAATGCAGTGCGTAG
GCAAGCTGAGGGCTTGTCTGAGGATGGGGCCGCAATGGCAGTGGAGCCAACTCAGATCCA
GCTCAGCAAGCGCTGGCGGGAATTGAGAGCAAATTTGCTCAGTTTCGAAGACTCAACTT
TGCACAAATTCACACTGTCCGTGAAGAAACGATGATGGTGATGACTGAAGACATGCCTTT
GGAAATTTCTTATGTGCCTTCTACTTATTTGACTGAAATCACTCATGTCTCACAAGCCCT
ATTAGAAGTGGAACAACTTCTCAATGCTCCTGACCTCTGTGCTAAGGACTTTGAAGATCT
CTTTAAGCAAGAGGAGTCTCTGAAGAATATAAAGATAGTCTACAACAAAGCTCAGGTCG
GATTGACATTATTCATAGCAAGAAGACAGCAGCATTGCAAAGTGCAACGCCTGTGGAAAG
GGTGAAGCTACAGGAAGCTCTCTCCCAGCTTGATTTCCAATGGGAAAAAGTTAACAAAAT
GTACAAGGACCGACAAGGGCGATTTGACAGATCTGTTGAGAAATGGCGGCGTTTTCATTA
TGATATAAAGATATTTAATCAGTGGCTAACAGAAGCTGAACAGTTTCTCAGAAAGACACA
AATTCCTGAGAATTGGAACATGCTAAATACAAATGGTATCTTAAGGAACTCCAGGATGG
CATTGGGCAGCGGCAAACTGTTGTCAGAACATTGAATGCAACTGGGGAAGAAATAATTCA
GCAATCCTCAAAAACAGATGCCAGTATTCTACAGGAAAAATTGGGAAGCCTGAATCTGCG
GTGGCAGGAGGTCTGCAAACAGCTGTCAGACAGAAAAAGAGGCTAGAAGAACAAAAGAA
TATCTTGTCAGAATTTCAAAGAGATTTAAATGAATTTGTTTTATGGTTGGAGGAAGCAGA
TAACATTGCTAGTATCCCACTTGAACCTGGAAAAGAGCAGCAACTAAAAGAAAAGCTTGA
GCAAGTCAAGTTACTGGTGGAAGAGTTGCCCCTGCGCCAGGGAATTCTCAAACAATTAAA
TGAAACTGGAGGACCCGTGCTTGTAAGTGCTCCCATAAGCCCAGAAGAGCAAGATAAACT
TGAAAATAAGCTCAAGCAGACAAATCTCCAGTGGATAAAGGTTTCCAGAGCTTTACCTGA
GAAACAAGGAGAAATTGAAGCTCAAATAAAAGACCTTGGGCAGCTTGAAAAAAGCTTGA
AGACCTTGAAGAGCAGTTAAATCATCTGCTGCTGTGGTTATCTCCTATTAGGAATCAGTT
GGAAATTTATAACCAACCAAACCAAGAAGGACCATTTGACGTTCAGGAAACTGAAATAGC
AGTTCAAGCTAAACAACCGGATGTGGAAGAGATTTTGTCTAAAGGGCAGCATTTGTACAA
GGAAAAACCAGCCACTCAGCCAGTGAAGAGGAAGTTAGAAGATCTGAGCTCTGAGTGGAA
GGCGGTAAACCGTTTACTTCAAGAGCTGAGGGCAAAGCAGCCTGACCTAGCTCCTGGACT
GACCACTATTGGAGCCTCTCCTACTCAGACTGTTACTCTGGTGACACAACCTGTGGTTAC
TAAGGAAACTGCCATCTCCAAACTAGAAATGCCATCTTCCTTGATGTTGGAGGTACCTGC
TCTGGCAGATTTCAACCGGGCTTGGACAGAACTTACCGACTGGCTTTCTCTGCTTGATCA
AGTTATAAAATCACAGAGGGTGATGGTGGGTGACCTTGAGGATATCAACGAGATGATCAT
CAAGCAGAAGGCAACAATGCAGGATTTGGAACAGAGGCGTCCCCAGTTGGAAGAACTCAT
TACCGCTGCCCAAAATTTGAAAAACAAGACCAGCAATCAAGAGGCTAGAACAATCATTAC
GGATCGAATTGAAAGAATTCAGAATCAGTGGGATGAAGTACAAGAACACCTTCAGAACCG
GAGGCAACAGTTGAATGAAATGTTAAAGGATTCAACACAATGGCTGGAAGCTAAGGAAGA
AGCTGAGCAGGTCTTAGGACAGGCCAGAGCCAAGCTTGAGTCATGGAAGGAGGGTCCCTA
TACAGTAGATGCAATCCAAAAGAAAATCACAGAAACCAAGCAGTTGGCCAAAGACCTCCG
CCAGTGGCAGACAAATGTAGATGTGGCAAATGACTTGGCCCTGAAACTTCTCCGGGATTA
TTCTGCAGATGATACCAGAAAAGTCCACATGATAACAGAGAATATCAATGCCTCTTGGAG
AAGCATTCATAAAGGGTGAGTGAGCGAGAGGCTGCTTGGAAGAAACTCATAGATTACT
GCAACAGTTCCCCCTGGACCTGGAAAAGTTTCTTGCCTGGCTTACAGAAGCTGAAACAAC
TGCCAATGTCCTACAGGATGCTACCCGTAAGGAAAGGCTCCTAGAAGACTCCAAGGGAGT
AAAAGAGCTGATGAAACAATGGCAAGACCTCCAAGGTGAAATTGAAGCTCACACAGATGT
TTATCACAACCTGGATGAAAACAGCCAAAAAATCCTGAGATCCCTGGAAGGTTCCGATGA
TGCAGTCCTGTTACAAAGACGTTTGGATAACATGAACTTCAAGTGGAGTGAACTTCGGAA
AAAGTCTCTCAACATTAGGTCCCATTTGGAAGCCAGTTCTGACCAGTGGAAGCGTCTGCA
CCTTTCTCTGCAGGAACTTCTGGTGTGGCTACAGCTGAAAGATGATGAATTAAGCCGGCA
GGCACCTATTGGAGGCGACTTTCCAGCAGTTCAGAAGCAGAACGATGTACATAGGGCCTT
CAAGAGGGAATTGAAAACTAAAGAACCTGTAATCATGAGTACTCTTGAGACTGTACGAAT
```

FIG. 5C

```
ATTTCTGACAGAGCAGCCTTTGGAAGGACTAGAGAAACTCTACCAGGAGCCCAGAGAGCT
GCCTCCTGAGGAGAGAGCCCAGAATGTCACTCGGCTTCTACGAAAGCAGGCTGAGGAGGT
CAATACTGAGTGGGAAAAATTGAACCTGCACTCCGCTGACTGGCAGAGAAAATAGATGA
GACCCTTGAAAGACTCCAGGAACTTCAAGAGGCCACGGATGAGCTGGACCTCAAGCTGCG
CCAAGCTGAGGTGATCAAGGGATCCTGGCAGCCCGTGGGCGATCTCCTCATTGACTCTCT
CCAAGATCACCTCGAGAAAGTCAAGGCACTTCGAGGAGAAATTGCGCCTCTGAAAGAGAA
CGTGAGCCACGTCAATGACCTTGCTCGCCAGCTTACCACTTTGGGCATTCAGCTCTCACC
GTATAACCTCAGCACTCTGGAAGACCTGAACACCAGATGGAAGCTTCTGCAGGTGGCCGT
CGAGGACCGAGTCAGGCAGCTGCATGAAGCCCACAGGGACTTTGGTCCAGCATCTCAGCA
CTTTCTTTCCACGTCTGTCCAGGGTCCTGGGAGAGAGCCATCTCGCCAAACAAAGTGCC
CTACTATATCAACCACGAGACTCAAACAACTTGCTGGGACCATCCCAAAATGACAGAGCT
CTACCAGTCTTTAGCTGACCTGAATAATGTCAGATTCTCAGCTTATAGGACTGCCATGAA
ACTCCGAAGACTGCAGAAGGCCCTTTGGCTTGGATCTCTTGAGCCTGTCAGCTGCATGTG
ATGCCTTGGACCAGCACAACCTCAAGCAAATGACCAGCCCATGGATATCCTGCAGATTA
TTAATTGTTTGACCACTATTTATGACCGCCTGGAGCAAGAGCACAACAATTTGGTCAACG
TCCCTCTCTGCGTGGATATGTGTCTGAACTGGCTGCTGAATGTTTATGATACGGGACGAA
CAGGGAGGATCCGTGTCCTGTCTTTTAAAACTGGCATCATTTCCCTGTGTAAAGCACATT
TGGAAGACAAGTACAGATACCTTTTCAAGCAAGTGGCAAGTTCAACAGGATTTTGTGACC
AGCGCAGGCTGGGCCTCCTTCTGCATGATTCTATCCAAATTCCAAGACAGTTGGGTGAAG
TTGCATCCTTTGGGGGCAGTAACATTGAGCCAAGTGTCCGGAGCTGCTTCCAATTTGCTA
ATAATAAGCCAGAGATCGAAGCGGCCCTCTTCCTAGACTGGATGAGACTGGAACCCCAGT
CCATGGTGTGGCTGCCCGTCCTGCACAGAGTGGCTGCTGCAGAAACTGCCAAGCATCAGG
CCAAATGTAACATCTGCAAAGAGTGTCCAATCATTGGATTCAGGTACAGGAGTCTAAAGC
ACTTTAATTATGACATCTGCCAAAGCTGCAAAAAACTGGTCGAGTTGCAAAAGGCCATA
AAATGCACTATCCCATGGTGGAATATTGCACTCCGACTACATCAGGAGAAGATGTTCGAG
ACTTTGCCAAGGTACTAAAAAACAAATTTCGAACCAAAAGGTATTTGCGAAGCATCCCC
GAATGGGCTACCTGCCAGTGCAGACTGTCTTAGAGGGGACAACATGGAAACTCCCGTTA
CTCTGATCAACTTCTGGCCAGTAGATTCTGCGCCTGCCTCGTCCCCTCAGCTTTCACACG
ATGATACTCATTCACGCATTGAACATTATGCTAGCAGGCTAGCAGAAATGGAAAACAGCA
ATGGATCTTATCTAAATGATAGCATCTCTCCTAATGAGAGCATAGATGATGAACATTTGT
TAATCCAGCATTACTGCCAAAGTTTGAACCAGGACTCCCCCCTGAGCCAGCCTCGTAGTC
CTGCCCAGATCTTGATTTCCTTAGAGAGTGAGGAAAGAGGGGAGCTAGAGAGAATCCTAG
CAGATCTTGAGGAAGAAAACAGGAATCTGCAAGCAGAATATGACCGTCTAAAGCAGCAGC
ACGAACATAAAGGCCTGTCCCCACTGCCGTCCCTCCTGAAATGATGCCCACCTCTCCCC
AGAGTCCCCGGGATGCTGAGCTCATTGCTGAGGCCAAGCTACTGCGTCAACACAAAGGCC
GCCTGGAAGCCAGGATGCAAATCCTGGAAGACCACAATAAACAGCTGGAGTCACAGTTAC
ACAGGCTAAGGCAGCTGCTGGAGCAACCCCAGGCAGAGGCCAAAGTGAATGGCACAACGG
TGTCCTCTCCTTCTACCTCTCTACAGAGGTCCGACAGCAGTCAGCCTATGCTGCTCCGAG
TGGTTGGCAGTCAAACTTCGGACTCCATGGGTGAGGAAGATCTTCTCAGTCCTCCCCAGG
ACACAAGCACAGGGTTAGAGGAGGTGATGGAGCAACTCAACAACTCCTTCCCTAGTTCAA
GAGGAAGAAATACCCCTGGAAAGCCAATGAGAGAGGACACAATGTAGGAACTCTTTTCCA
CATGGCAGATGATTTGGGCAGAGCGATGGAGTCCTTAGTATCAGTCATGACAGATGAAGA
AGGAGCAGAATAAATGTTTTACAACTCCTGATTCCCGCATGGTTTTATAATATTCATAC
AACAAAGAGGATTAGACAGTAAGAGTTTACAAGAAATAAATCTATATTTTGTGAAGGGT
AGTGGTATTATACTGTAGATTTCAGTAGTTTCTAAGTCTGTTATTGTTTTGTTAACAATG
GCAGGTTTTACACGTCTATGCAATTGTACAAAAAAGTTATAAGAAAACTACATGTAAAAT
CTTGATAGCTAAATAACTTGCCATTTCTTTATATGGAACGCATTTTGGGTTGTTTAAAAA
TTTATAACAGTTATAAGAAAGATTGTAAACTAAAGTGTGCTTTATAAAAAAAGTTGTT
TATAAAAACCCCTAAAAACAAAACAAACACACACACACACATACACACACACACAA
```

FIG. 5D

```
AACTTTGAGGCAGCGCATTGTTTTGCATCCTTTTGGCGTGATATCCATATGAAATTCATG
GCTTTTTCTTTTTTTGCATATTAAAGATAAGACTTCCTCTACCACCACACCAAATGACTA
CTACACACTGCTCATTTGAGAACTGTCAGCTGAGTGGGGCAGGCTTGAGTTTTCATTTCA
TATATCTATATGTCTATAAGTATATAAATACTATAGTTATATAGATÀAAGAGATACGAAT
TTCTATAGACTGACTTTTTCCATTTTTTAAATGTTCATGTCACATCCTAATAGAAAGAAA
TTACTTCTAGTCAGTCATCCAGGCTTACCTGCTTGGTCTAGAATGGATTTTTCCCGGAGC
CGGAAGCCAGGAGGAAACTACACCACACTAAAACATTGTCTACAGCTCCAGATGTTTCTC
ATTTTAAACAACTTTCCACTGACAACGAAAGTAAAGTAAAGTATTGGATTTTTTTAAAGG
GAACATGTGAATGAATACACAGGACTTATTATATCAGAGTGAGTAATCGGTTGGTTGGTT
GATTGATTGATTGATTGATACATTCAGCTTCCTGCTGCTAGCAATGCCACGATTTAGATT
TAATGATGCTTCAGTGGANNTCAATCAGAAGGTATTCTGACCTTGTAACATCAGAAGGT
ATTTTTTAACTCCCCAAGCAGTAGCAGGACGATGATAGGGCTGGAGGGCTATGGATTCCC
AGCCCATCCCTGTGAAGGAGTAGGCCACTCTTTAAGTGAAGGATTGGATGATTGTTCATA
ATACATAAAGTTCTCTGTAATTACAACTAAATTATTATGCCCKCTTCTCACAGTCAAAAG
GAACTGGGTGGTTTGGTTTTTGNNNNTTTTTTAGATTTTTTGTCCCATGTGGGATGAGTT
TTTAAATGCCACAAGACATAATTTAAAATAAATAAACTTTGGGAAAAGGTGTAAGACAGT
AGCCCCATCACATTTGTGATACTGACAGGTATCAACCCAGAAGCCCATGAACTGTGTTTC
CATCCTTTGCATTTCTCTGCGAGTAGTTCCACACAGGTTTGTAAGTAAGTAAGAAAGAAG
GCAAATTGATTCAAATGTTACAAAAAACCCTTCTTGGTGGATTAGACAGGTTAAATATA
TAAACAAACAAACAAAAATTGCTC
```

FIG. 5E

```
                                  **  *       *       *      *              *
HUMAN                    GGGATTCCCTCACTTTCCCCCTACAGGACTCAGATC
MOUSE                    CCTCACTCACTTGCCCCTTACAGGACTCAGCTC

*  *       ** *  *****                   *  **         *          *
     TGGGAGGCAATTACCTTCGGAGAAAAACGAATAGGAAAAACTGAAGTGTTACTTTTTTT-
     TTGAAGGCAATAGCTTTATAGAAAAAACGAATAGGAAGACTTGAAGTGCTATTTTTTTTT

***********    *                *    *     *   ***         *
     -----------AAAGCTGCTGAAGTTTGTTGGTTTCTCATTGTTTTAAGCCTACTGGAG
     TTTTTTTTGTCAAGGCTGCTGAAGTTTATTGGCTTCTCATCGTACCTAAGCCTCCTGGAG

**  *  *             *  *   **  *                    ***
     CAATAAAGTTTGAAG-AACTTTTACCAGGTTTTTTTTATCGCTGCCTTGATATACAC----
     CAATAAAACTGGGAGAAACTTTTACCAAGATTTTT--ATCCCTGCCTTGATATATACTTT

*    *
201  -TTTTCAAAATGCTTTGGTGGGAAGAAGTAGAGGACTGTTATGAAAGAGAAGATGTTCAA
              M  L  W  W  E  E  V  E  D  C  Y  E  R  E  D  V  Q
              M  L  W  W  E  E  V  E  D  C  Y  E  R  E  D  V  Q
212  TTTTTCCAAATGCTTTGGTGGGAAGAAGTAGAGGACTGTTATGAAAGAGAAGATGTTCAA

*                            *     *  *  *
     AAGAAAACATTCACAAAATGGGTAAATGCACAATTTTCTAAGTTTGGGAAGCAGCATATT
      K  K  T  F  T  K  W │V│ N  A  Q  F  S  K  F  G  K  Q  H  I
      K  K  T  F  T  K  W │I│ N  A  Q  F  S  K  F  G  K  Q  H  I
     AAGAAAACATTCACAAAATGGATAAATGCACAATTTTCTAAGTTTGGAAAGCAACACATA

*                 *              *  **                    *  *       *
     GAGAACCTCTTCAGTGACCTACAGGATGGGAGGCGCCTCCTAGACCTCCTCGAAGGCCTG
     │E│ N  L  F  S  D  L  Q  D  G │R│ R  L  L  D  L  L  E  G  L
     │D│ N  L  F  S  D  L  Q  D  G │K│ R  L  L  D  L  L  E  G  L
     GACAACCTCTTCAGTGACCTGCAGGATGGAAAACGCCTCCTAGACCTCTTGGAAGGCCTT

*        *
     ACAGGGCAAAAACTGCCAAAAGAAAAAGGATCCACAAGAGTTCATGCCCTGAACAATGTC
      T  G  Q  K  L  P  K  E  K  G  S  T  R  V  H  A  L  N  N  V
      T  G  Q  K  L  P  K  E  K  G  S  T  R  V  H  A  L  N  N  V
     ACAGGGCAAAAACTGCCAAAAGAAAAGGGATCTACAAGAGTTCATGCCCTGAACAATGTC

*  *       *                                    *        *
     AACAAGGCACTGCGGGTTTTGCAGAACAATAATGTTGATTTAGTGAATATTGGAAGTACT
      N  K  A  L  R  V  L  Q │N│ N  N  V  D  L  V  N  I  G  S  T
      N  K  A  L  R  V  L  Q │K│ N  N  V  D  L  V  N  I  G  S  T
     AACAAGGCACTGCGGGTCTTACAGAAAAATAATGTTGATTTAGTGAATATAGGAAGCACT

*  *           *
500  GACATCGTAGATGGAAATCATAAACTGACTCTTGGTTTGATTTGGAATATAATCCTCCAC
      D  I  V  D  G  N  H  K  L  T  L  G  L  I  W  N  I  I  L  H
      D  I  V  D  G  N  H  K  L  T  L  G  L  I  W  N  I  I  L  H
512  GACATAGTGGATGGAAATCATAAACTCACTCTTGGTTTGATTTGGAATATAATCCTCCAC
```

FIG.7A-1

```
                    *                      *                                      *
         TGGCAGGTCAAAAATGTAATGAAAAATATCATGGCTGGATTGCAACAAACCAACAGTGAA
         W  Q  V  K  N  V  M  K │N│ I  M  A  G  L  Q  Q  T  N  S  E
         W  Q  V  K  N  V  M  K │T│ I  M  A  G  L  Q  Q  T  N  S  E
         TGGCAGGTCAAAAATGTGATGAAAACTATCATGGCTGGATTGCAGCAAACCAACAGTGAA

*                  *        *                          *    *
         AAGATTCTCCTGAGCTGGGTCCGACAATCAACTCGTAATTATCCACAGGTTAATGTAATC
         K  I  L  L  S  W  V  R  Q  S  T  R  N  Y  P  Q  V  N  V  I
         K  I  L  L  S  W  V  R  Q  S  T  R  N  Y  P  Q  V  N  V  I
         AAGATTCTTCTGAGCTGGGTTCGACAGTCAACACGTAATTATCCACAGGTTAACGTCATC

*   *         *   *  **                           *           *
         AACTTCACCACCAGCTGGTCTGATGGCCTGGCTTTGAATGCTCTCATCCATAGTCATAGG
         N  F  T │T│ S  W  S  D  G  L  A  L  N  A  L  I  H  S  H  R
         N  F  T │S│ S  W  S  D  G  L  A  L  N  A  L  I  H  S  H  R
         AACTTCACCTCTAGCTGGTCCGACGGGTTGGCTTTGAATGCTCTTATCCATAGTCACAGG

*         *      *                  **         *               *     *
         CCAGACCTATTTGACTGGAATAGTGTGGTTTGCCAGCAGTCAGCCACACAACGACTGGAA
         P  D  L  F  D  W  N  S  V  V │C│ Q │Q│ S  A  T  Q  R  L  E
         P  D  L  F  D  W  N  S  V  V │S│ Q │H│ S  A  T  Q  R  L  E
         CCCGACCTGTTTGATTGGAATAGTGTGGTTTCACAGCACTCAGCCACCCAAAGACTGGAA

*
   800   CATGCATTCAACATCGCCAGATATCAATTAGGCATAGAGAAACTACTCGATCCTGAAGAT
         H  A  F  N  I  A  R  Y  Q  L  G  I  E  K  L  L  D  P  E  D
         H  A  F  N
   812   CATGCCTTCAACA

GTTGATACCACCTATCCAGATAAGAAGTCCATCTTAATGTACATCACATCACTCTTCCAA
         V  D  T  T  Y  P  D  K  K  S  I  L  M  Y  I  T  S  L  F  Q

GTTTTGCCTCAACAAGTGAGCATTGAAGCCATCCAGGAAGTGGAAATGTTGCCAAGGCCA
         V  L  P  Q  Q  V  S  I  E  A  I  Q  E  V  E  M  L  P  R  P

CCTAAAGTGACTAAAGAAGAACATTTTCAGTTACATCATCAAATGCACTATTCTCAACAG
         P  K  V  T  K  E  E  H  F  Q  L  H  H  Q  M  H  Y  S  Q  Q

ATCACGGTCAGTCTAGCACAGGGATATGAGAGAACTTCTTCCCCTAAGCCTCGATTCAAG
         I  T  V  S  L  A  Q  G  Y  E  R  T  S  S  P  K  P  R  F  K

1100  ┌─AGCTATGCCTACACACAGGCTGCTTATGTCACCACCTCTGACCCTACACGGAGCCCATTT
         S  Y  A  Y  T  Q  A  A  Y  V  T  T  S  D  P  T  R  S  P  F

CCTTCACAGCATTTGGAAGCTCCTGAAGACAAGTCATTTGGCAGTTCATTGATGGAGAGT
         P  S  Q  H  L  E  A  P  E  D  K  S  F  G  S  S  L  M  E  S
```

FIG.7A-2

```
GAAGTAAACCTGGACCGTTATCAAACAGCTTTAGAAGAAGTATTATCGTGGCTTCTTTCT
E   V   N   L   D   R   Y   Q   T   A   L   E   E   V   L   S   W   L   L   S

GCTGAGGACACATTGCAAGCACAAGGAGAGATTTCTAATGATGTGGAAGTGGTGAAAGAC
A   E   D   T   L   Q   A   Q   G   E   I   S   N   D   V   E   V   V   K   D

CAGTTTCATACTCATGAGGGGTACATGATGGATTTGACAGCCCATCAGGGCCGGGTTGGT
Q   F   H   T   H   E   G   Y   M   M   D   L   T   A   H   Q   G   R   V   G
```
1400 
```
AATATTCTACAATTGGGAAGTAAGCTGATTGGAACAGGAAAATTATCAGAAGATGAAGAA
N   I   L   Q   L   G   S   K   L   I   G   T   G   K   L   S   E   D   E   E

ACTGAAGTACAAGAGCAGATGAATCTCCTAAATTCAAGATGGGAATGCCTCAGGGTAGCT
T   E   V   Q   E   Q   M   N   L   L   N   S   R   W   E   C   L   R   V   A

AGCATGGAAAAACAAAGCAATTTACATAGAGTTTTAATGGATCTCCAGAATCAGAAACTG
S   M   E   K   Q   S   N   L   H   R   V   L   M   D   L   Q   N   Q   K   L

AAAGAGTTGAATGACTGGCTAACAAAAACAGAAGAAAGAACAAGGAAAATGGAGGAAGAG
K   E   L   N   D   W   L   T   K   T   E   E   R   T   R   K   M   E   E   E

CCTCTTGGACCTGATCTTGAAGACCTAAAACGCCAAGTACAACAACATAAGGTGCTTCAA
P   L   G   P   D   L   E   D   L   K   R   Q   V   Q   Q   H   K   V   L   Q
```
1699

FIG.7A-3

Mouse

```
1  AGAGTTATGCCTTCACACAGGCTGCTTATGTTGCCACCTCTGATTCCACACAGAGCCCCT
      S  Y  A  F  T  Q  A  A  Y  V  A  T  S  D  S  T  Q  S  P  Y
   ATCCTTCACAGCATTTGCAAGCTCCCAGAGACAAGTCACTTGACAGTTCATTGATGGAGA
      P  S  Q  H  L  E  A  P  R  D  K  S  L  D  S  S  L  M  E  T
   CGGAAGTAAATCTGGATAGTTACCAAACTGCTTTAGAAGAAGTACTTTCATGGCTTCTTT
      E  V  N  L  D  S  Y  Q  T  A  L  E  E  V  L  S  W  L  L  S
   CTGCCGAGGATACATTGCGAGCACAAGGAGAGATTTCAAATGATGTTGAAGAAGTAAAG
      A  E  D  T  L  R  A  Q  G  E  I  S  N  D  V  E  E  V  K  E
   AACAGTTTCATGCTCATGAGGGATTCATGATGGATCTGACATCTCATCAAGGACTTGTTG
      Q  F  H  A  H  E  G  F  M  M  D  L  T  S  H  Q  G  L  V  G
   GTAATGTTCTACAGTTAGGAAGTCAACTAGTTGGAAAAGGGAAATTATCAGAAGATGAAG
      N  V  L  Q  L  G  S  Q  L  V  G  K  G  K  L  S  E  D  E  E
   AAGCTGAAGTGCAAGAACAAATGAATCTCCTAAATTCAAGATGGGAATGTCTCAGGGTAG
      A  E  V  Q  E  Q  M  N  L  L  N  S  R  W  E  C  L  R  V  A
   CTAGCATGGAAAAACAAAGCAAATTACACAAAGTTCTAATGGATCTCCAGAATCAGAAAT
      S  M  E  K  Q  S  K  L  H  K  V  L  M  D  L  Q  N  Q  K  L
   TAAAAGAACTAGATGACTGGTTAACAAAAACTGAAGAGAGAACTAAGAAAATGGAGGAAG
      K  E  L  D  D  W  L  T  K  T  E  E  R  T  K  K  M  E  E  E
```

Mouse

```
   AGCCCTTTGGACCTGATCTTGAAGATCTAAAATGCCAAGTACAACAACATAAGGTGCTT
      P  F  G  P  D  L  E  D  L  K  C  Q  V  Q  Q  H  K  V  L
                                         1  Q  Q  H  K  V  L
                                      1  ACAACAACATAAGGTGCTT
                                             Human
```

```
                  *  *  *            *  *              *  *  *
   CAAGAAGATCTAGAACAGGAGCAGGTCAGGGTCAACTCGCTCACTCACATGGTAGTAGTG
      Q  E  D  L  E  Q  E  Q  V  R  V  N  S  L  T  H  M  V  V  V
      Q  E  D  L  E  Q  E  Q  V  R  V  N  S  L  T  H  M  V  V  V
   CAAGAAGATCTAGAACAAGAACAAGTCAGGGTCAATTCTCTCACTCACATGGTGGTGGTA

*  *  *      *    *                            *
   GTTGATGAATCCAGCGGTGATCATGCAACAGCTGCTTTGGAAGAACAACTTAAGGTACTG
      V  D  E  S  S  G  D  H  A  T  A  A  L  E  E  Q  L  K  V  L
      V  D  E  S  S  G  D  H  A  T  A  A  L  E  E  Q  L  K  V  L
   GTTGATGAATCTAGTGGAGATCACGCAACTGCTGCTTTGGAAGAACAACTTAAGGTATTG

*           *                 *        *  *        *
   GGAGATCGATGGGCAAATATCTGCAGATGGACTGAAGACCGCTGGATTGTTTTACAAGAT
      G  D  R  W  A  N  I  C  R  W  T  E  D  R  W |I  V| L  Q  D
      G  D  R  W  A  N  I  C  R  W  T  E  D  R  W |V  L| L  Q  D
   GGAGATCGATGGGCAAACATCTGTAGATGGACAGAAGACCGCTGGGTTCTTTTACAAGAC

*        *       *  *  *                                 *
   ATTCTTCTAAAATGGCAGCATTTTACTGAAGAACAGTGCCTTTTTAGTACATGGCTTTCA
      I  L  L  K  W  Q |H  F| T  E  E  Q  C  L  F  S |T| W  L  S
      I  L  L  K  W  Q |R  L| T  E  E  Q  C  L  F  S |A| W  L  S
   ATCCTTCTCAAATGGCAACGTCTTACTGAAGAACAGTGCCTTTTTAGTGCATGGCTTTCA
```

FIG.7B-1

```
                  *    * *        *         *
     GAAAAAGAAGATGCAATGAAGAACATTCAGACAAGTGGCTTTAAAGATCAAAATGAAATG
     E K E D A M K N I Q T S G F K D Q N E M
     E K E D A V N K I H T T G F K D Q N E M
     GAAAAGAAGATGCAGTGAACAAGATTCACACAACTGGCTTTAAAGATCAAAATGAAATG

* *           *       * ** ***     ***                    * *
     ATGTCAAGTCTTCACAAAATATCTACTTTAAAAATAGATCTAGAAAAGAAAAAGCCAACC
     M S S L H K I S T L K I D L E K K K P T
     L S S L Q K L A V L K A D L E K K K Q S
     TTATCAAGTCTTCAAAAACTGGCCGTTTTAAAAGCGGATCTAGAAAAGAAAAAGCAATCC

**      ***             *        *    **           *
     ATGGAAAAACTAAGTTCACTCAATCAAGATCTACTTTCGGCACTGAAAAATAAGTCAGTG
     M E K L S L N Q D L L S A L K N K S V
     M G K L Y S L N Q D L L S T L K N K S V
     ATGGGCAAACTGTATTCACTCAAACAAGATCTTCTTTCAACACTGAAGAATAAGTCAGTG

*      *    ***    *      *      * ***      *    **
     ACTCAAAAGATGGAAATCTGGATGGAAAACTTTGCACAACGTTGGGACAATTTAACCCAA
     T Q K M E I W M E N F A Q R W D N L T Q
     T Q K T E A W L D N F A R C W D N L V Q
     ACCCAGAAGACGGAAGCATGGCTGGATAACTTTGCCCGGTGTTGGGACTATTTAGTCCAA

*          *                           *    **
     AAACTTGAAAAGAGTTCAGCACAAATTTCACAGGCTGTCACCACCACTCAACCATTCCTA
     K L E K S S A Q I S Q A V T T T Q P F L
     K L E K S T A Q I S Q A V T T T Q P S L
     AAACTTGAAAAGAGTACAGCACAGATTTCACAGGCTGTCACCACCACTCAGCCATCACTA

*           *                   *    *
     ACACAGACAACTGTAATGGAAACGGTAACTATGGTGACCACAAGGGAACAAATCATGGTA
     T Q T T V M E T V T M V T T R E Q I M V
     T Q T T V M E T V T T V T T R E Q I L V
     ACACAGACAACTGTAATGGAAACAGTAACTACGGTGACCACAAGGGAACAGATCCTGGTA

*     *                       *                     *
     AAACATGCCCAAGAGGAACTTCCACCACCACCTCCTCAAAAGAAGAGGCAGATAACTGTG
     K H A Q E E L P P P P P Q K K R Q I T V
     K H A Q E E L P P P P P Q K K R Q I T V
     AAGCATGCTCAAGAGGAACTTCCACCACCACCTCCCCAAAAGAAGAGGCAGATTACTGTG

* *                   *                  *
     GATTCTGAACTCAGGAAAAGGTTGGATGTCGATATAACTGAACTTCACAGTTGGATTACT
     D S E L R K R L D V D I T E L H S W I T
     D S E I R K R L D V D I T E L H S W I T
     GATTCTGAAATTAGGAAAAGGTTGGATGTTGATATAACTGAACTTCACAGCTGGATTACT

*        *    *             *        *     * *         *
     CGTTCAGAAGCTGTATTACAGAGTTCTGAATTTGCAGTCTATCGAAAAGAAGGCAACATC
     R S E A V L Q S S E F A V Y R K E G N I
     R S E A V L Q S P E F A I F R K E G N F
     CGCTCAGAAGCTGTGTTGCAGAGTCCTGAATTTGCAATCTTTCGGAAGGAAGGCAACTTC
```

FIG.7B-2

```
              **                          **                   *
      TCAGACTTGCAAGAAAAAGTCAATGCCATAGCACGAGAAAAAGCAGAGAAGTTCAGAAAA
      S  D  L  Q  E  K  V  N  A  I  A  R  E  K  A  E  K  F  R  K
      S  D  L  K  E  K  V  N  A  I  E  R  E  K  A  E  K  F  R  K
      TCAGACTTAAAAGAAAAAGTCAATGCCATAGAGCGAGAAAAAGCTGAGAAGTTCAGAAAA

**
      CTGCAAGATGCCAGCAGATCAGCTCAGGCCCTGGTGGAACAGATGGCAAATGAGGGTGTT
      L  Q  D  A  S  R  S  A  Q  A  L  V  E  Q  M  A  N  E  G  V
      L  Q  D  A  S  R  S  A  Q  A  L  V  E  Q  M  V  N  E  G  V
      CTGCAAGATGCCAGCAGATCAGCTCAGGCCCTGGTGGAACAGATGGTGAATGAGGGTGTT

*   *   *      *         *                      **
      AATGCTGAAAGTATCAGACAAGCTTCAGAACAACTGAACAGCCGGTGGACAGAATTCTGC
      N  A  E  S  I  R  Q  A  S  E  Q  L  N  S  R  W  T  E  F  C
      N  A  D  S  I  K  Q  A  S  E  Q  L  N  S  R  W  I  E  F  C
      AATGCAGATAGCATCAAACAAGCCTCAGAACAACTGAACAGCCGGTGGATCGAATTCTGC

*       *          *          *         *  *    ** *   *
      CAATTGCTGAGTGAGAGAGTTAACTGGCTAGAGTATCAAACCAACATCATTACCTTTTAT
      Q  L  L  S  E  R  V  N  W  L  E  Y  Q  T  N  I  I  T  F  Y
      Q  L  L  S  E  R  L  N  W  L  E  Y  Q  N  N  I  I  A  F  Y
      CAGTTGCTAAGTGAGAGACTTAACTGGCTGGAGTATCAGAACAACATCATCGCTTTCTAT

*                        *        *           *
      AATCAGCTACAACAATTGGAACAGATGACAACTACTGCCGAAAACTTGTTGAAAACCCAG
      N  Q  L  Q  Q  L  E  Q  M  T  T  T  A  E  N  L  L  K  T  Q
      N  Q  L  Q  Q  L  E  Q  M  T  T  T  A  E  N  W  L  K  I  Q
      AATCAGCTACAACAATTGGAGCAGATGACAACTACTGCTGAAAACTGGTTGAAAATCCAA

*  *         *                               *
      TCTACCACCCTATCAGAGCCAACAGCAATTAAAAGCCAGTTAAAAATTTGTAAGGATGAA
      S  T  T  L  S  E  P  T  A  I  K  S  Q  L  K  I  C  K  D  E
      P  T  T  P  S  E  P  T  A  I  K  S  Q  L  K  I  C  K  D  E
      CCCACCACCCCATCAGAGCCAACAGCAATTAAAAGTCAGTTAAAAATTTGTAAGGATGAA

*  **  *       *            *         * *      *  ** ***
      GTCAACAGATTGTCAGCTCTTCAGCCTCAAATTGAGCAATTAAAAATTCAGAGTCTACAA
      V  N  R  L  S  A  L  Q  P  Q  I  E  Q  L  K  I  Q  S  L  Q
      V  N  R  L  S  G  L  Q  P  Q  I  E  R  L  K  I  Q  S  I  A
      GTCAACCGGCTATCAGGTCTTCAACCTCAAATTGAACGATTAAAAATTCAAAGCATAGCC

*  *        *   *  *       *                              *
      CTGAAAGAAAAGGGACAGGGGCCAATGTTTCTGGATGCAGACTTTGTGGCCTTTACTAAT
      L  K  E  K  G  Q  G  P  M  F  L  D  A  D  F  V  A  F  T  N
      L  K  E  K  G  Q  G  P  M  F  L  D  A  D  F  V  A  F  T  N
      CTGAAAGAGAAAGGACAAGGACCCATGTTCCTGGATGCAGACTTTGTGGCCTTTACAAAT

*  **       ** *     **        *
      CATTTTAACCACATCTTTGATGGTGTGAGGGCCAAAGAGAAAGAGCTACAGACAATTTTT
      H  F  N  H  I  F  D  G  V  R  A  K  E  K  E  L  Q  T  I  F
      H  F  K  Q  V  F  S  D  V  Q  A  K  E  K  E  L  Q  T  I  F
      CATTTTAAGCAAGTCTTTTCTGATGTGCAGGCCAGAGAGAAAGAGCTACAGACAATTTTT

FIG.7B-3
```

```
          *                          *        **           *     *
GACACTTTACCACCAATGCGCTATCAGGAGACAATGAGTAGCATCAGGACGTGGATCCAG
D   T   L   P   P   M   R   Y   Q   E   T   M   S  [S]  I   R   T   W  [I]  Q
D   T   L   P   P   M   R   Y   Q   E   T   M   S  [A]  I   R   T   W  [V]  Q
GACACTTTGCCACCAATGCGCTATCAGGAGACCATGAGTGCCATCAGGACATGGGTCCAG

*             **       *  *              *     *     *              *
CAGTCAGAAAGCAAACTCTCTGTACCTTATCTTAGTGTTACTGAATATGAAATAATGGAG
Q   S   E  [S]  K   L   S  [V]  P  [Y]  L   S   V   T  [E]  Y   E   I   M   E
Q   S   E  [T]  K   L   S  [I]  P  [Q]  L   S   V   T  [D]  Y   E   I   M   E
CAGTCAGAAACCAAACTCTCCATACCTCAACTTAGTGTCACCGACTATGAAATCATGGAG

*                *            *      * *                  *              *  *
GAGAGACTCGGGAAATTACAGGCTCTGCAAAGTTCTTTGAAAGAGCAACAAAATGGCTTC
[E]  R   L   G  [K]  L   Q   A   L   Q   S   S   L  [K]  E   Q   Q  [N]  G  [F]
[Q]  R   L   G  [E]  L   Q   A   L   Q   S   S   L  [Q]  E   Q   Q  [S]  G  [L]
CAGAGACTCGGGGAATTGCAGGCTTTACAAAGTTCTCTGCAAGAGCAACAAAGTGGCCTA

*              * ***             *       * *           *     *     *    **   *
AACTATCTGAGTGACACTGTGAAGGAGATGGCCAAGAAAGCACCTTCAGAAATATGCCAG
[N]  Y   L   S  [D]  T   V   K   E   M  [A]  K   K   A   P   S   E   I  [C]  Q
[Y]  Y   L   S  [T]  T   V   K   E   M  [S]  K   K   A   P   S   E   I  [S]  R
TACTATCTCAGCACCACTGTGAAAGAGATGTCGAAGAAAGCGCCCTCTGAAATTAGCCGG

**                *          * *           *  *             *
AAATATCTGTCAGAATTTGAAGAGATTGAGGGGCACTGGAAGAAACTTTCCTCCCAGTTG
K   Y  [L]  S   E   F   E   E   I   E   G  [H]  W   K   K   L   S   S   Q   L
K   Y  [Q]  S   E   F   E   E   I   E   G  [R]  W   K   K   L   S   S   Q   L
AAATATCAATCAGAATTTGAAGAAATTGAGGGACGCTGGAAGAAGCTCTCCTCCCAGCTG

*  ****    *                *  *   *                  *        *
GTGGAAAGCTGCCAAAAGCTAGAAGAACATATGAATAAACTTCGAAAATTCAGAATTCAC
V   E  [S]  C   Q   K   L   E   E  [H]  M   N   K   L   R   K  [F]  Q   N   H
V   E  [H]  C   Q   K   L   E   E  [Q]  M   N   K   L   R   K  [I]  Q   N   H
GTTGAGCATTGTCAAAAGCTAGAGGAGCAAATGAATAAACTCCGAAAAATCAGAATTCAC

*    *  **                                            *     *
ATAAAAACCTTACAGAAATGGATGGCTGAAGTTGATGTTTTCCTGAAAGAGGAATGGCCT
I  [K]  T   L  [Q]  K   W   M   A   E   V   D   V   F   L   K   E   E   W   P
I  [Q]  T   L  [K]  K   W   M   A   E   V   D   V   F   L   K   E   E   W   P
ATCCAAACCCTGAAGAAATGGATGGCTGAAGTTGATGTTTTCTGAAGGAGGAATGGCCT

*          * **          *     *        *     *        *              **
GCCCTGGGGGATGCTGAAATCCTGAAAAAACAGCTCAAACAATGCAGACTTTTAGTTGGT
A   L   G   D  [A]  E   I   L   K   K   Q   L   K   Q   C   R   L   L   V  [G]
A   L   G   D  [S]  E   I   L   K   K   Q   L   K   Q   C   R   L   L   V  [S]
GCCCTTGGGGATTCAGAAATTCTAAAAAAGCAGCTGAAACAGTGCAGACTTTTAGTCAGT

*                   *     *     *
GATATTCAAACAATTCAGCCCAGTTTAAATAGTGTTAATGAAGGTGGGCAGAAGATAAAG
D   I   Q   T   I   Q   P   S   L   N   S   V   N   E   G   G   Q   K   I   K
D   I   Q   T   I   Q   P   S   L   N   S   V   N   E   G   G   Q   K   I   K
GATATTCAGACAATTCAGCCCAGTCTAAACAGTGTCAATGAAGGTGGGCAGAAGATAAAG
```

FIG.7B-4

```
             *       * * **           * *       *            * *   *
     AGTGAAGCTGAACTTGAGTTTGCATCCAGACTGGAGACAGAACTTAGAGAGCTTAACACT
     S  E  A  E  L  E  F  A  S  R  L  E  T  E  L  R  E  L  N  T
     N  E  A  E  P  E  F  A  S  R  L  E  T  E  L  K  E  L  N  T
     AATGAAGCAGAGCCAGAGTTTGCTTCGAGACTTGAGACAGAACTCAAAGAACTTAACACT

*    **       **        *     *     *
     CAGTGGGATCACATATGCCGCCAGGTCTACACCAGAAAGGAAGCCTTAAAGGCAGGTTTG
     Q  W  D  H  I  C  R  Q  V  Y  T  R  K  E  A  L  K  A  G  L
     Q  W  D  H  M  C  Q  Q  V  Y  A  R  K  E  A  L  K  G  G  L
     CAGTGGGATCACATGTGCCAACAGGTCTATGCCAGAAAGGAGGCCTTGAAGGGAGGTTTG

*        *           *                    * *
     GATAAAACCGTAAGCCTCCAAAAAGATCTATCAGAGATGCATGAGTGGATGACACAAGCT
     D  K  T  V  S  L  Q  K  D  L  S  E  M  H  E  W  M  T  Q  A
     E  K  T  V  S  L  Q  K  D  L  S  E  M  H  E  W  M  T  Q  A
     GAGAAAACTGTAAGCCTCCAGAAAGATCTATCAGAGATGCACGAATGGATGACACAAGCT

*       *                                    * *   *
     GAAGAAGAATATCTAGAGAGAGATTTTGAATATAAAACTCCAGATGAATTACAGACTGCT
     E  E  E  Y  L  E  R  D  F  E  Y  K  T  P  D  E  L  Q  T  A
     E  E  E  Y  L  E  R  D  F  E  Y  K  T  P  D  E  L  Q  K  A
     GAAGAAGAGTATCTTGAGAGAGATTTTGAATATAAAACTCCAGATGAATTACAGAAAGCA

*                        *
     GTTGAAGAAATGAAGAGAGCTAAAGAAGAGGCACTACAAAAAGAAACTAAAGTGAAACTC
     V  E  E  M  K  R  A  K  E  E  A  L  Q  K  E  T  K  V  K  L
     V  E  E  M  K  R  A  K  E  E  A                717
     GTTGAAGAGATGAAGAGAGCTAAAGAAGAGGCCC              2153

CTTACTGAGACTGTAAATAGTGTAATAGCTCACGCTCCACCCTCAGCACAAGAGGCCTTA
     L  T  E  T  V  N  S  V  I  A  H  A  P  P  S  A  Q  E  A  L
     AAAAAGGAACTTGAAACTCTGACCACCAACTACCAATGGCTGTGCACCAGGCTGAATGGA
     K  K  E  L  E  T  L  T  T  N  Y  Q  W  L  C  T  R  L  N  G
     AAATGCAAAACTTTGGAAGAAGTTTGGGCATGTTGGCATGAGTTATTGTCATATTTAGAG
     K  C  K  T  L  E  E  V  W  A  C  W  H  E  L  L  S  Y  L  E
     AAAGCAAACAAGTGGCTCAATGAAGTAGAATTGAAACTTAAAACCATGGAAAATGTTCCT
     K  A  N  K  W  L  N  E  V  E  L  K  L  K  T  M  E  N  V  P
     GCAGGACCTGAGGAAATCACTGAAGTGCTAGAATCTCTTGAAAATCTGATGCATCATTCA
     A  G  P  E  E  I  T  E  V  L  E  S  L  E  N  L  M  H  H  S
     GAGGAGAACCCAAATCAGATTCGTCTATTGGCACAGACTCTTACAGATGGAGGAGTCATG
     E  E  N  P  N  Q  I  R  L  L  A  Q  T  L  T  D  G  G  V  M
     GATGAACTGATCAATGAGGAGCTTGAGACGTTTAATTCTCGTTGGAGGGAACTACATGAA
     D  E  L  I  N  E  E  L  E  T  F  N  S  R  W  R  E  L  H  E
     GAGGCTGTGAGGAAACAAAAGTTGCTTGAACAGAGTATCCAGTCTGCCCAGGAAATTGAA
     E  A  V  R  K  Q  K  L  L  E  Q  S  I  Q  S  A  Q  E  I  E
     AAGTCCTTGCACTTAATTCAGGAGTCGCTTGAATTC       3273
     K  S  L  H  L  I  Q  E  S  L  E  F
```

Nucleic Acid Homology    (2153, 1885)    87.552%
    Amino Acid Homology      (717, 621)      86.611%

FIG.7B-5

```
MLWWEEVEDCYEREDVQKKTFTKWVNAQFSKFGKQHIENLFSDLQDGRRLLDLLEGLTGQ
KLPKEKGSTRVHALNNVNKALRVLQNNNVDLVNIGSTDIVDGNHKLTLGLIWNIILHWQV
KNVMKNIMAGLQQTNSEKILLSWVRQSTRNYPQVNVINFTTSWSDGLALNALIHSHRPDL
FDWNSVVCQQSATQRLEHAFNIARYQLGIEKLLDPEDVDTTYPDKKSILMYITSLFQVLP
QQVSIEAIQEVEMLPRPPKVTKEEHFQLHHQMHYSQQITVSLAQGYERTSSPKPRFKSYA
YTQAAYVTTSDPTRSPFPSQHLEAPEDKSFGSSLMESEVNLDRYQTALEEVLSWLLSAED
TLQAQGEISNDVEVVKDQFHTHEGYMMDLTAHQGRVGNILQLGSKLIGTGKLSEDEETEV
QEQMNLLNSRWECLRVASMEKQSNLHRVLMDLQNQKLKELNDWLTKTEERTRKMEEEPLG
PDLEDLKRQVQQHKVLQEDLEQEQVRVNSLTHMVVVVDESSGDHATAALEEQLKVLGDRW
ANICRWTEDRWVLLQDILLKWQRLTEEQCLFSAWLSEKEDAVNKIHTTGFKDQNEMLSSL
QKLAVLKADLEKKKQSMGKLYSLKQDLLSTLKNKSVTQKTEAWLDNFARCWDNLVQKLEK
STAQISQAVTTTQPSLTQTTVMETVTTVTTREQILVKHAQEELPPPPPQKKRQITVDSEI
RKRLDVDITELHSWITRSEAVLQSPEFAIFRKEGNFSDLKEKVNAIEREKAEKFRKLQDA
SRSAQALVEQMVNEGVNADSIKQASEQLNSRWIEFCQLLSERLNWLEYQNNIIAFYNQLQ
QLEQMTTTAENWLKIQPTTPSEPTAIKSQLKICKDEVNRLSGLQPQIERLKIQSIALKEK
GQGPMFLDADFVAFTNHFKQVFSDVQAREKELQTIFDTLPPMRYQETMSAIRTWVQQSET
KLSIPQLSVTDYEIMEQRLGELQALQSSLQEQQSGLYYLSTTVKEMSKKAPSEISRKYQS
EFEEIEGRWKKLSSQLVEHCQKLEEQMNKLRKIQNHIQTLKKWMAEVDVFLKEEWPALGD
SEILKKQLKQCRLLVSDIQTIQPSLNSVNEGGQKIKNEAEPEFASRLETELKELNTQWDH
MCQQVYARKEALKGGLEKTVSLQKDLSEMHEWMTQAEEEYLERDFEYKTPDELQKAVEEM
KRAKEEAQQKEAKVKLLTESVNSVIAQAPPVAQEALKKELETLTTNYQWLCTRLNGKCKT
LEEVWACWHELLSYLEKANKWLNEVEFKLKTTENIPGGAEEISEVLDSLENLMRHSEDNP
NQIRILAQTLTDGGVMDELINEELETFNSRWRELHEEAVRRQKLLEQSIQSAQETEKSLH
LIQESLTFIDKQLAAYIADKVDAAQMPQEAQKIQSDLTSHEISLEEMKKHNQGKEAAQRV
LSQIDVAQKKLQDVSMKFRLFQKPANFELRLQESKMILDEVKMHLPALETKSVEQEVVQS
QLNHCVNLYKSLSEVKSEVEMVIKTGRQIVQKKQTENPKELDERVTALKLHYNELGAKVT
ERKQQLEKCLKLSRKMRKEMNVLTEWLAATDMELTKRSAVEGMPSNLDSEVAWGKATQKE
IEKQKVHLKSITEVGEALKTVLGKKETLVEDKLSLLNSNWIAVTSRAEEWLNLLLEYQKH
METFDQNVDHITKWIIQADTLLDESEKKKPQQKEDVLKRLKAELNDIRPKVDSTRDQAAN
LMANRGDHCRKLVEPQISELNHRFAAISHRIKTGKASIPLKELEQFNSDIQKLLEPLEAE
IQQGVNLKEEDFNKDMNEDNEGTVKELLQRGDNLQQRITDERKREEIKIKQQLLQTKHNA
LKDLRSQRRKKALEISHQWYQYKRQADDLLKCLDDIEKKLASLPEPRDERKIKEIDRELQ
KKKEELNAVRRQAEGLSEDGAAMAVEPTQIQLSKRWREIESKFAQFRRLNFAQIHTVREE
TMMVMTEDMPLEISYVPSTYLTEITHVSQALLEVEQLLNAPDLCAKDFEDLFKQEESLKN
IKDSLQQSSGRIDIIHSKKTAALQSATPVERVKLQEALSQLDFQWEKVNKMYKDRQGRFD
RSVEKWRRFHYDIKIFNQWLTEAEQFLRKTQIPENWEHAKYKWYLKELQDGIGQRQTVVR
TLNATGEEIIQQSSKTDASILQEKLGSLNLRWQEVCKQLSDRKKRLEEQKNILSEFQRDL
NEFVLWLEEADNIASIPLEPGKEQQLKEKLEQVKLLVEELPLRQGILKQLNETGGPVLVS
APISPEEQDKLENKLKQTNLQWIKVSRALPEKQGEIEAQIKDLGQLEKKLEDLEEQLNHL
LLWLSPIRNQLEIYNQPNQEGPFDVQETEIAVQAKQPDVEEILSKGQHLYKEKPATQPVK
RKLEDLSSEWKAVNRLLQELRAKQPDLAPGLTTIGASPTQVTVTLVTQPVVTKETAISKLE
MPSSLMLEVPALADFNRAWTELTDWLSLLDQVIKSQRVMVGDLEDINEMIIKQKATMQDL
EQRRPQLEELITAAQNLKNKTSNQEARTIITDRIERIQNQWDEVQEHLQNRRQQLNEMLK
DSTQWLEAKEEAEQVLGQARAKLESWKEGPYTVDAIQKKITETKQLAKDLRQWQTNVDVA
NDLALKLLRDYSADDTRKVTMITENINASWRSIHKRVSEREAALEETHRLLQQFPLDLEK
FLAWLTEAETTANVLQDATRKERLLEDSKGVKELMKWQDLQGEIEAHTDVYHNLDENSQ
KILRSLEGSDDAVLLQRRLDNMNFKWSELRKKSLNIRSHLEASSDQWKRLHLSLQELLVW
LQLKDDELSRQAPIGGDFPAVQKQNDVHRAFKRELKTKEPVIMSTLETVPIFLTEQPLEG
LEKLYQEPRELPPEERAQNVTRLLRKQAEEVNTEWEKLNLHSADWQRKIDETLERLQELQ
```

FIG. 8A

```
EATDELDLKLRQAEVIKGSWQPVGDLLIDSLQDHLEKVKALRGEIAPLKENVSHVNDLAR
QLTTLGIQLSPYNLSTLEDLNTRWKLLQVAVEDRVRQLHEAHRDFGPASQHFLSTSVQGP
WERAISPNKVPYYINHETQTTCWDHPKMTELYQSLADLNNVRFSAYRTAMKLRRLQKALC
LDLLSLSAACDALDQHNLKQNDQPMDILQIINCLTTIYDRLEQEHNNLVNVPLCVDMCLN
WLLNVYDTGRTGRIRVLSFKTGIISLCKAHLEDKYRYLFKQVASSTGFCDQRRLGLLLHD
SIQIPRQLGEVASFGGSNIEPSVRSCFQFANNKPEIEAALFLDWMRLEPQSMVWLPVLHR
VAAAETAKHQAKCNICKECPIIGFRYRSLKHFNYDICQSCKKTGRVAKGHKMHYPMVEYC
TPTTSGEDVRDFAKVLKNKFRTKRYFAKHPRMGYLPVQTVLEGDNMETPVTLINFWPVDS
APASSPQLSHDDTHSRIEHYASRLAEMENSNGSYLNDSISPNESIDDEHLLIQHYCQSLN
QDSPLSQPRSPAQILISLESEERGELERILADLEEENRNLQAEYDRLKQQHEHKGLSPLP
SPPEMMPTSPQSPRDAELIAEAKLLRQHKGRLEARMQILEDHNKQLESQLHRLRQLLEQP
QAEAKVNGTTVSSPSTSLQRSDSSQPMLLRVVGSQTSDSMGEEDLLSPPQDTSTGLEEVM
EQLNNSFPSSRGRNTPGKPMREDTMI
```

DYSTROPHIN →

1 2 3 4 5 6 7 8 9 10 11 12 13 14 15 16 17

DYSTROPHIN →

1 2 3 4 5 6 7 8 9 10 11 12 13 14 15 16 17

ANTIBODIES TO DYSTROPHIN AND USES THEREFOR

BACKGROUND OF THE INVENTION

The work reported herein was supported by grants from the United States government including N.I.H. grants HD 18658 and NS23740. The government has certain rights in this invention.

This application is a continuation of application Ser. No. 07/971,057 filed Nov. 3, 1992, abandoned, which is a Continuation of Ser. No. 07/136,618, filed Dec. 22, 1987, now U.S. Pat. No. 5,239,060 which is a Continuation-in-Part of Ser. No. 06/890,694, filed Jul. 25, 1986 (abandoned).

This invention relates to the detection and treatment of hereditary disease, and in particular to the detection and diagnosis of Duchenne, Becker and Outlier muscular dystrophies (MD) by various methods.

Duchenne muscular dystrophy (DMD) is an X-linked recessive genetic disorder which affects about 1 in 3,300 males. Traits associated with DMD (DMD) phenotype) are well known and may include elevated creatine phosphokinase levels in serum (at least 10× the normal level), delayed development of motor function, and muscle weakness characterized by the replacement of muscle fiber with adipose and fibrose tissue accompanied by a marked variation in muscle size. Until recently, carrier identification in DMD families generally was accomplished by detecting elevated levels of creatine phosphokinase in serum.

Becker muscular dystrophy (BMD) is also an X-linked recessive genetic disorder, but occurs at only 10% of the frequency of DMD. BMD is a more benign form of muscular dystrophy which follows a less rapid clinical course than DMD. Both DMD and BMD are caused by mutations in the DMD gene located in the Xp21 region of the short arm of the human X chromosome.

Outlier muscular dystrophy (OMD) is a mild Duchenne/severe Becker disorder. It forms a subgroup that comprises approximately 10 percent of individuals inflicted with DMD.

Restriction fragment length polymorphisms (RFLPs) occur when the genomic DNA sequence in a population of animals varies such that complete digestion with a restriction endonuclease will result in a set of restriction fragments of one or more different size arrays. The differences are due to the presence or absence in the DNA sequence of sites recognized by the endonuclease; a sequence in which the site is present will be cut by the endonuclease giving one array, and a sequence in which the site is not present will fail to be cut by the endonuclease, giving another array.

It has been shown that RFLPs which are located near a gene associated with a hereditary disease can be used to determine the likelihood of a particular person having a defective gene and thus having the disease. Bakker et al., The Lancet, Mar. 23, 1985, at 655 describes "eleven RFLP-markers . . . on the short arm of the X chromosome [that] are useful in the diagnosis of DMD since they bridge the Duchenne locus at genetic distances varying between 3 and 20 centiMorgans."

SUMMARY OF THE INVENTION

Applicants have cloned 14 kb of human cDNA substantially corresponding to the MD gene, and parts of the surrounding genomic DNA. Applicants have also isolated and characterized cDNA corresponding to the homologous locus in the mouse. Dystrophin, the polypeptide product of the human MD locus, and its mouse homologue (mMD), has been identified using antibodies directed against fusion polypeptides containing two distinct regions of MD and mMD cDNA. Parts of the complete MD cDNA and surrounding genomic DNA were also used to define RFLPs in the Xp21 region of the short arm of the X chromosome that are useful in diagnosis of MD mutations.

In a first aspect, the invention features an MD probe having a substantially purified single-stranded nucleic acid sequence capable of selectively hybridizing to a region of DNA on a human X chromosome between the deletion break point at Xp21.3 (defined below) and the translocation break point at X;11 (defined below). "Selectively hybridizing" means hybridizing to the desired sequence under conditions that are sufficiently stringent to generally prevent hybridization to other sequences encountered in the sample. "Substantially purified" or "substantially pure" means a substance that is sufficiently separated from other elements of the environment in which it naturally occurs to function in assays according to the invention.

In preferred embodiments, the nucleic acid sequence is incapable of selectively hybridizing to other parts of the short arm of the X chromosome, i.e., the region of DNA between the deletion break point at Xp21.3 and the p terminus of the X chromosome, and to the region of DNA between the translocation break point at X;11 and the centromere of the X chromosome.

In an additional preferred embodiment, the MD probe has a nucleic acid sequence of at least 10 base pairs in length from a portion of the sequence of any one of the six cDNA probes, that together span the 14 kb cDNA corresponding to the human MD gene, deposited on Jul. 15, 1987 with the A.T.C.C. under the twelve access numbers 57666 to 57677, inclusive. Each probe is deposited in a vector in *E. coli* and in the form of a purified plasmid. Hence, each probe is available under two access numbers.

In a second aspect, the invention features an MD probe having a substantially purified single-stranded nucleic acid sequence capable of selectively hybridizing to at least a part of the human MD gene. The human MD gene, as used herein, is that portion of human DNA on the short arm of the X chromosome in which a mutation can give rise to an MD phenotype. Exons in this DNA are substantially represented by the 14 kb cDNA deposit discussed below. The sequence for most of this cDNA is depicted in FIGS. 5A–5E. The invention also includes probes directed to or derived from genomic DNA, including intronic sequences in the MD gene.

In preferred embodiments, the nucleic acid probe sequence is incapable of selectively hybridizing to regions of DNA outside the MD gene.

The probe of the invention can be used for analyzing a sample of genomic DNA of a human subject for the presence of a mutant MD gene.

In a third aspect, the invention features a method for diagnosing muscular dystrophy in human patients involving contacting the probes outlined above with a sample and detecting whether these probes hybridize to nucleic acid in the sample.

In preferred embodiments, a series of probes is used in the method of diagnosis, in which the series, in combination, spans a 14 kb sequence of MD DNA or RNA, encompassing an MD gene. For example, probes according to the invention are used for detecting RFLPs that are closely associated (linked) with mutations in the MD gene causing an MD phenotype. "Closely associated" means that the likelihood of a genetic recombination event occurring between the sites of an RFLP and a MID mutation is very low (less than 5%). The advantage of such probes is that one can use them to predict, with a high degree of confidence, the probability that an individual (within a family with a history of MD) having a particular RFLP phenotype will also have an MD mutation.

In a fourth aspect, the invention features a substantially pure mammalian polypeptide, dystrophin, encoded by an MD gene. This polypeptide has both human and murine forms. The invention also includes substantially pure polypeptides that are immunologically cross-reactive with dystrophin, or which have substantially the same amino acid sequence as a 15 amino acid sequence of dystrophin. By "polypeptide" we mean to include large polypeptides and proteins. "Substantially the same" means that the amino acids in such a sequence may be substituted by other amino acids having equivalent side groups, i.e., conservative substitutions are permissible.

Two polypeptides are immunologically cross-reactive if they are bound to the same specific antibody or family of specific antibodies. Particularly useful types of cross-reactive polypeptides are those that can be used to challenge an animal to produce an antibody that reacts with dystrophin. The invention also includes polypeptides that are useful for competitive assays, i.e., polylpeptides that compete with dystrophin for binding sites on specific antibodies.

In a fifth aspect, the invention features substantially purified nucleic acid encoding dystrophin, or polypeptides immunologically cross-reactive with dystrophin.

A preferred embodiment of this nucleic acid comprises an approximately 14 kb pair sequence of cDNA or RNA corresponding to a nucleic acid sequence of a MD gene, or fragments thereof greater than 45 bases. This nucleic acid may correspond to a human MD gene or a murine Dmd gene.

In a sixth aspect, the invention features antibodies to dystrophin or polypeptides that are immunologically cross-reactive with dystrophin.

The invention also includes the use of these antibodies in a method of immunodiagnosis for MD involving contacting a sample of tissue (particularly muscle tissue) with one of these antibodies and detecting the presence of antibody-dystrophin complexes. Complexes that indicate the presence of dystrophin of normal size and abundance in such tissue generally indicate the absence of MD. This aspect of the invention includes the numerous well-known formats of immunodiagnostics, such as ELISA, and Western blots. In one embodiment, this method is performed by comparing the molecular weight (M.W.) of dystrophin, or fragments thereof, that are detected in the complex to the molecular weight of a normal control dystrophin polypeptide. In this method, the presence of fragments of dystrophin, i.e., dystrophin of abnormal size, or the complete absence of detectable dystrophin, indicates MD. A normal control is established by repeated analyses of the dystrophin polypeptide found in normal individuals without MD or individuals without MD related dystrophins.

In general, the normal dystrophin polypeptide is approximately 400,000 daltons in size and is absent or undetectable in DMD patients. However, BMD patients and a small percentage of patients diagnosed as those with DMD exhibit dystrophin of an abnormal size, i.e., in the form of smaller M.W. fragments.

In a preferred embodiment, this method features the additional step of comparing the molecular weight of the sample antigenic polypeptide to the molecular weight of BMD and DMD controls. In this method diagnosis of DMD is made in the presence of a pattern comparable to the DMD control, diagnosis of BMD is made in the presence of a pattern comparable to the BMD control, and the absence of MD is indicated by a pattern comparable to the normal control. The BMD and DMD controls are established by repeated assays of dystrophin in muscle samples in patients diagnosed as having BMD or DMD. The molecular weight of the dystrophin or fragments thereof are determined for each type of MD and are recorded and averaged to create a control pattern. A pattern "comparable" to these controls is a pattern that is identical to, or sufficiently similar to, these controls to allow a diagnosis of one type of MD, i.e., either BMD or DMD.

The invention also features a method of therapy for MD involving the insertion of cDNA, or a fragment thereof, corresponding to the MD gene into a vector and reintroducing these genetically altered cells back into the patient. The cells are injected into the bloodstream or muscle tissue to produce dystrophin in an amount effective to control the degeneration of muscle fibers and to control the proliferation of connective tissue within muscle fibers.

The methods of the invention can be used for prenatal (fetal) screening as well as in the detection of heterozygotic individuals carrying MD gene mutations but exhibiting no symptoms.

Other features and advantages of the invention will be apparent from the following description of the preferred embodiments thereof, and from the claims.

DESCRIPTION OF THE PREFERRED EMBODIMENTS

The Figures will first briefly be described.

Drawings FIG. 1f is a standard ISCN (1981) ideogram of the p terminal end (pter) of the human X chromosome showing the approximate positions of cloned DNA fragments and specific deletion and translocation break points;

FIG. 3 is the DNA sequence of two parts of the MD gene used as probes of the invention;

FIGS. 5A–5E shows 13 kb of the 14 kb nucleotide sequence corresponding to the human MD gene.

FIGS. 7A and 7B are partial nucleotide and predicted amino acid sequences of human and murine MD cDNAs;

FIGS. 8A–8B are the amino acid sequence of the dystrophin polypeptide.

HUMAN MD PROBES AND NUCLEIC ACID

Probes of the invention contain nucleic acid homologous to DNA of the MD gene or to DNA from a region of DNA close to the MD gene. A description of the DNA region containing segments to which the probes are homologous follows.

Figure 1:
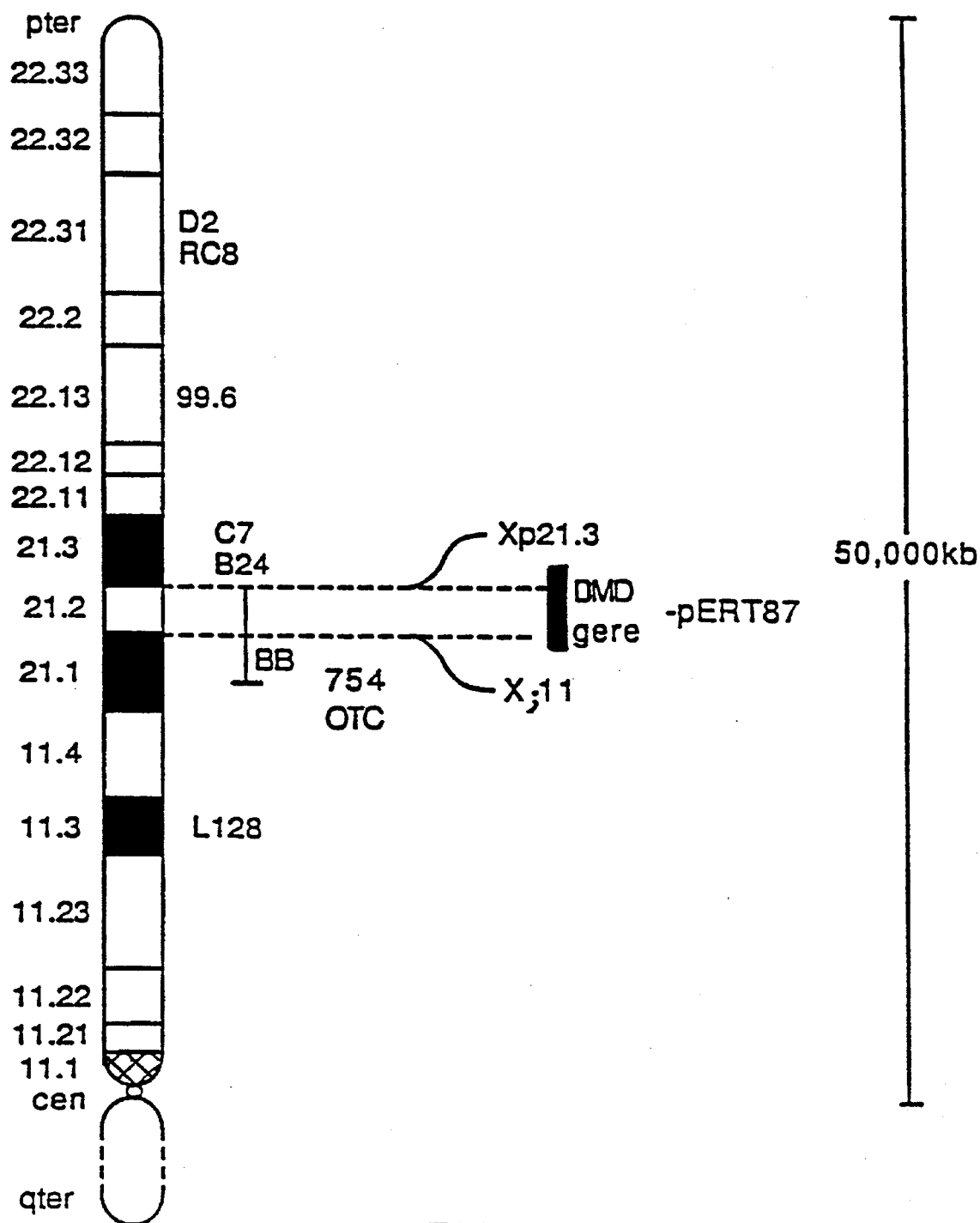

Referring to FIG. 1, the approximate positions of previously cloned regions of the human X chromosome (D2, RC8, 99.6, 754, OTC C7, B24, and L128) are shown relative to a standard (ISCN 1981) ideogram of the short arm (p) of the human X chromosome. Also shown is the region of DNA deletion in the X chromosome of a male patient (BB) suffering from three X-linked disorders, including DMD; the deletion is described by Francke et al., Am. J. Hum. Genet. 37:250 (1985), and the cell line is available from Human Genetic Mutant Cell Repository in Camden, N.J. (cell line repository number GM7947A). The deletion is defined by two break points in the DNA, Xp21.3 and Xp21.1. Also marked is a break point X;11 (p. 21.1; a 13.5), which is attributable to the balanced reciprocal translocation described by Greenstein et al., Cytog. Cell Genet. 27:268 (1980) (cell line available from Human Genetic Mutant Cell Repository in Camden, N.J., cell line repository identification number GM1695).

Break points Xp21.3 and X;11 approximately define the boundaries of the DMD gene, which lies within the Xp21.2 chromosome band region. More specifically, the MD gene extends approximately $1 \times 10^6$ bp beyond both the BB deletion breakpoint towards the p terminus and beyond the X;11 translocation breakpoint toward the centromere.

Following are examples of probes and nucleic acids suitable in this invention. These examples are not limiting to the invention and those skilled in the art will recognize other methods suitable to obtain such probes. In particular, the probes described below can be used to probe other libraries of other animals to isolate equivalent DNA or RNA.

EXAMPLE 1 pERT87, A Genomic Clone

In order to isolate the probes of the invention, a library of DNA from around the MD gene area was constructed by enriching for this DNA using differential hybridization. The procedure is described in detail by Kunkel et al., PNAS 87:4778 (1985). Accordingly, 250 µg of DNA from the male patient BB was isolated, sheared by sonication to a mean size of 1,000 base pairs (bp), and hybridized to 1.25 µg of Mbo-1 cleaved DNA from a 49, XXXXY lymphoid cell line (GM1202), as described by Palmer et al., Cell 37:171 (1984). The DNAs were then heated to 100° C. for 5 minutes, cooled on ice, and added to a final reaction volume of 2.5 ml of 7% phenol. The mixture was shaken intermittently for 37 h over a 5 day period (Kohne et al., Biochemistry 16:5329 (1977)). After chloroform extraction and dialysis to remove salts, the hybridized DNA was ethanol precipitated. These conditions allow Mbo-1 fragments from the 49, XXXXY DNA, with no complementary sequence in the deleted DNA region of the BB male, to self-hybridize and thus be cloned as Mbo-1 fragments. 5 µg of the precipitated DNA was ligated to 0.1 µg BamH1-cleaved dephosphorylated pBR322 and transformed into E. coli strain MC1061. (The BamH1 ends are compatible in ligation with the Mbo-1 ends of the chromosomal DNA.) 3,000 colonies were isolated.

As described by Kunkel et al., supra, the isolated colonies were screened using standard techniques to determine which one contained DNA that hybridized with DNA from normal individuals but not with DNA from the male BB. One clone, pERT87, hybridized to a 1.1 kb HindIII fragment of normal human DNA, but not to BB DNA. The intensity of hybridization was dependent upon the X chromosome content of the DNA being probed. Hybridization was also detected in a rodent-human hybrid cell line having an intact human X chromosome, but not with a cell line having DNA only from the human chromosome region Xp11.3 to Xqter. Thus, the cloned region in pERT87 is on the short arm (p) of the X chromosome. Three other clones gave similar results, although each clone hybridizes to a different HindIII fragment.

The clones were analyzed for their ability to hybridize with DNA from a variety of cell lines having deletions or translocations of the human X chromosome. pERT87 was localized to DNA within the Xp21-Xp22 region. The location of pERT87 was determined by its lack of hybridization to the region Xp21-Xter (using cell line X;11) and to the region p21-pter (using a cell line with a break point at Xp21.3, Fryns et al., Clin., Genet. 22:76, (1982)), and by its hybridization to the region Xp22-Xqter (using a cell line described by Mahandas et al., PNAS 76:5779 (1979)).

As described in Monaco et al., Nature 316:842 (1985), pERT87 was used to probe the DNA of 57 unrelated DMD males. pERT87 did not hybridize to DNA from five of the males indicating that they had deletions of DNA around the cloned DNA in pERT87. Assuming that the DMD phenotype in these five males results from deletions within the MD gene, this result provides evidence that pERT87 contains DNA homologous to a region of DNA within the MD gene.

EXAMPLE 2 pERT87 Derivatives

In order to isolate more DNA from the MD region, two human genomic libraries were screened with pERT87 by the procedure described in Monaco, supra; one was constructed in Charon 35 (Loenan et al., Gene 26:171 (1983)) and one in EMBL-3 (Frischauf et al., J. Molec. Biol. 170:827 (1983). Using standard techniques, chromosomal "walks" were performed in both directions from the region homologous to pERT87 using pERT87 as a probe for the above libraries. Five bacteriophage clones, including W1 and W2-R in FIG. 4, were isolated, and small unique-sequence subclones, in pBR322, pUC18 or Blue-Scribe (Stratagene), were constructed. These subclones were restriction mapped and small fragments free of human repetitive elements identified. Unique sequence subclones near the extreme ends of the human inserts in these clones were used as probes for the next walking step in the same libraries. Three of these subclones, pERT87-18, -8, and -1 contained DNA absent from the above five DMD boys with genomic deletions. These subclones span an area of 38 kb. Further chromosome walks in the EMBL-3 library extended the cloned area to 220 kb (shown in FIGS. 2 and 4). These clones include pERT87-15, -14, and -27.

Figure 4:
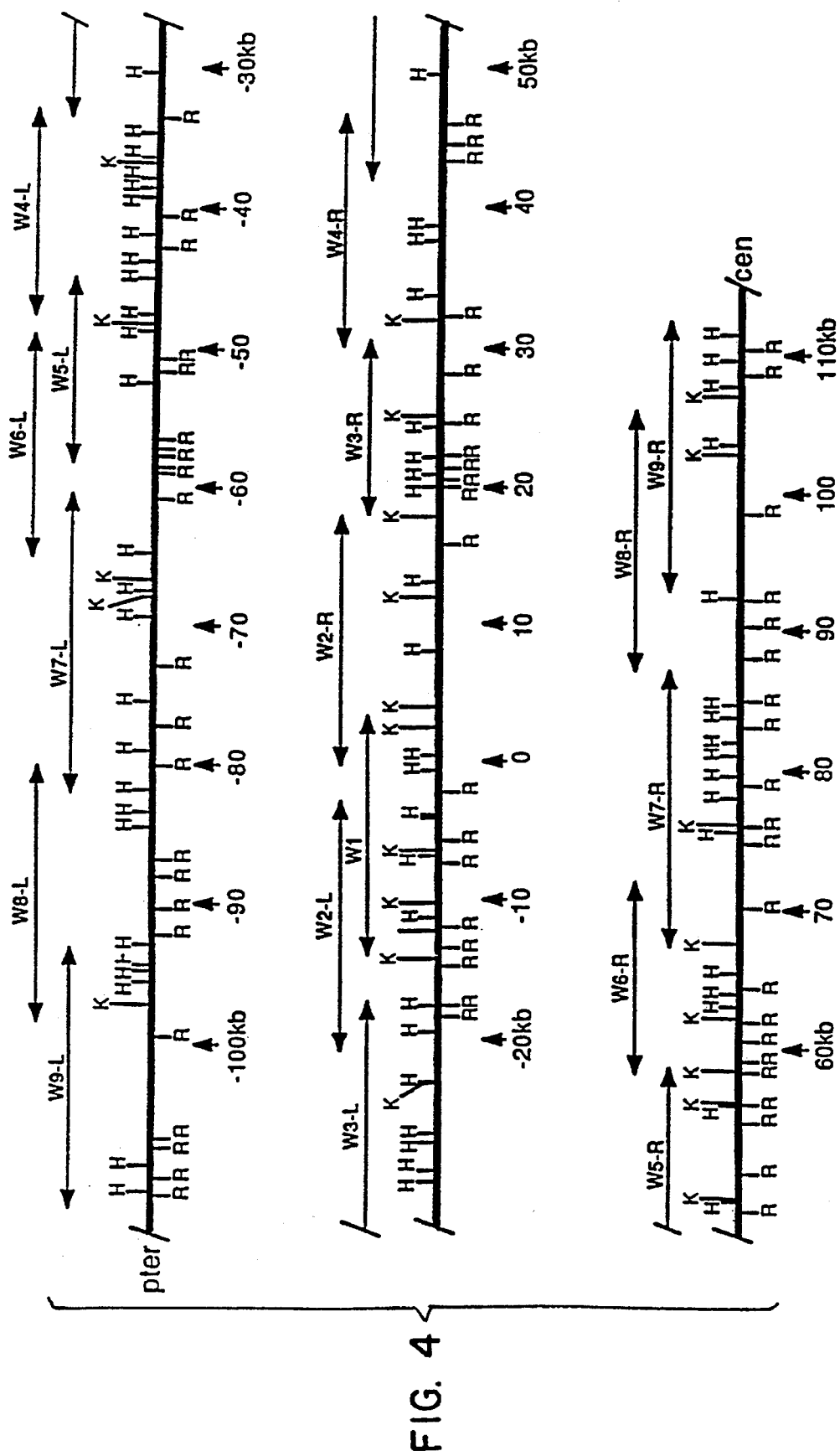
FIG. 4 is a diagrammatic representation of 220 kb of cloned DNA showing the location and size of cloned DNA isolated from librares of human chromosomal DNA.

To determine the positions of these cloned regions relative to the MD gene, chromosomal DNA was isolated from 53 boys with DMD or the related disease, Becker muscular dystrophy (BMD)—the gene for which is also located within band Xp21—who have deleted areas of DNA in their X chromosome. This DNA was tested, using standard Southern blot analysis (see below), against the subclones in order to determine the break points of the DNA deletions in the 53 boys relative to the cloned DNA. This was simply done by first ordering the subclones as shown in FIG. 4, and then determining which subclones contained DNA present in the deleted chromosomes (thus being outside the break point) and those which contained DNA not present in the deleted chromosome (thus having DNA within the break point). Subclones that are positioned between these two types of subclones and have DNA present in the deleted chromosomes, must have DNA in which the deletion break point occurred. Once localized to a region within the cloned DNA, the break points were further localized within 100–1,000 bp using restriction enzyme analysis. The results of these experiments are summarized in FIG. 2.

Figure 2:
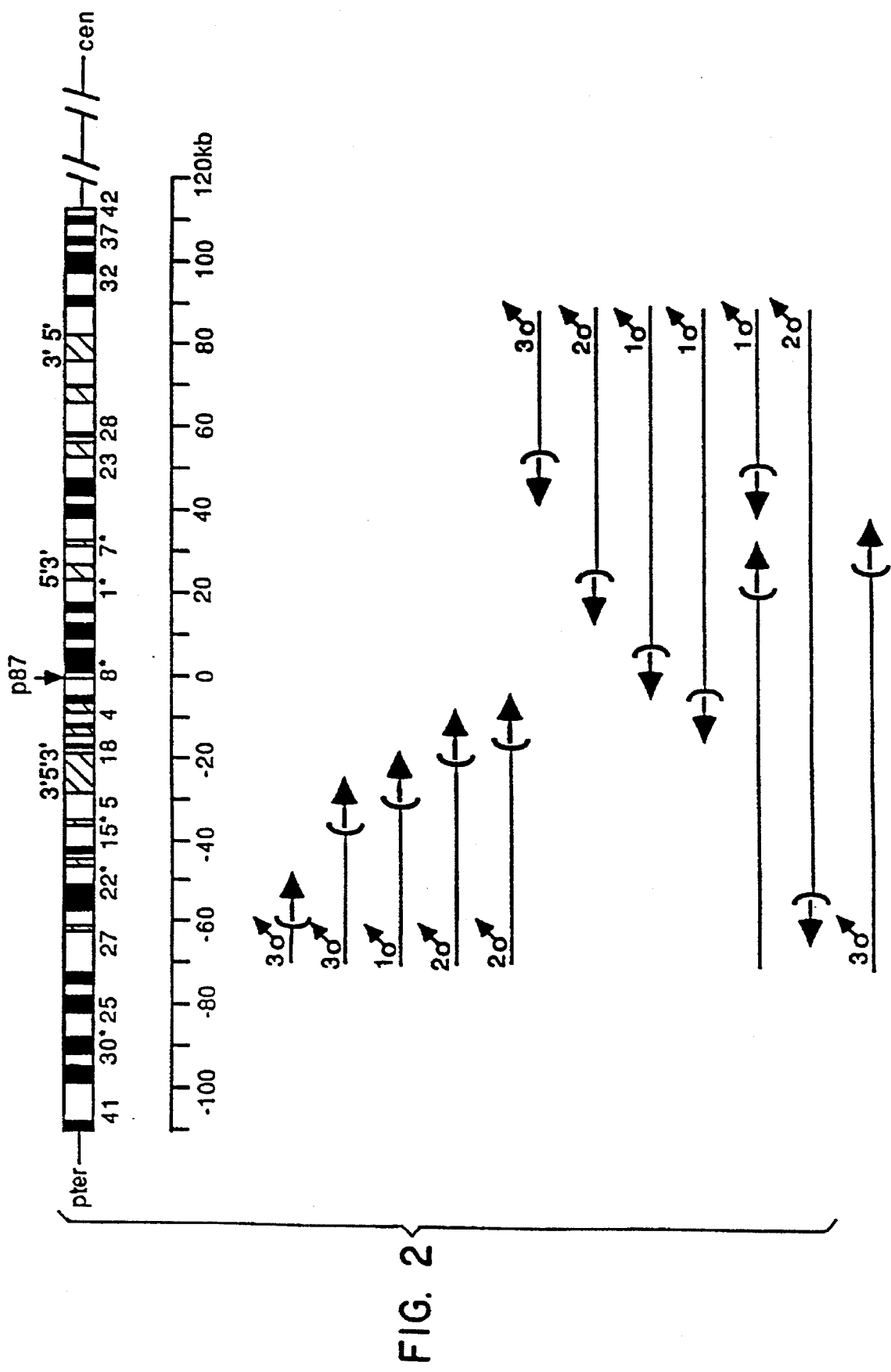
FIG. 2 is a diagrammatic representation of 220 kb of cloned DNA from the human Xp21 chromosome, showing regions deleted in some DMD human males.

FIG. 2 depicts a schematic drawing of 220 kb of contiguous human genomic DNA with a kb scale. The darkened blocks represent regions of repeated sequences, cross hatched boxes represent moderately repeated sequences, and open boxes represent unique sequences. Numbers below these blocks represent pERT87 subclones. Line sequences are represented by an L, as described in Singer, Cell 28:433 (1981). As shown in FIG. 2, fourteen deletions were found to break at the left side of the cloned DNA and extend in a rightward direction (see arrows) towards the centromere. Nine deletions were found that extend in the opposite direction. The majority of the deletions have independent break points, but for simplicity the deletions have been schematically presented together in FIG. 2. Since the deletion breaks, which give rise to a DMD or BMD phenotype, occur within the pERT87 region and extend in both directions, this analysis demonstrates that pERT87 and the subclones are clearly within the MD gene.

The profile in FIG. 2 indicates that the MD gene is located on a large segment of DNA. The fact that large deletions resulting from mutations in the gene yield a DMD phenotype similar to that found in other DMD boys who do not have deletions indicates that the gene product can be either completely missing or aberrant yet still yield a similar clinical picture. The gene responsible lies on a very large segment of X chromosome DNA, and is estimated to be approximately 2,000 kb (FIG. 1).

Referring to FIG. 3, the DNA sequence of several subclones are determined by standard procedures, using dideoxy analysis. Representative sequences from pERT87-4 (upper sequence) and -25 (lower sequence) are presented. Probes suitable for the invention can readily be synthesized from any parts of these sequences, or any other parts of the 14 kb cDNA sequence corresponding to an MD gene described below. Such probes can also be used for further chromosome walking.

EXAMPLE 3 cDNA

Standard Northern analysis of RNA from a variety of human fetal and adult tissues revealed a single mRNA estimated to be 16 kb from the total RNA or polyA-selected RNA of fetal skeletal muscle which hybridizes to pERT87-25. This approximately 16 kb transcript is the mRNA coding for the product of the MD gene. It is possible to isolate this mRNA, using standard hybridization techniques, and the probes of the invention, and to prepare a cDNA library from it. The clones in this cDNA library are suitable as probes of the invention, and for isolating other clones by chromosome walking in human genomic DNA libraries by standard techniques towards intronic DNA in the MD gene and to the X;11 and Xp21.3 break points.

For example, by using standard techniques, an oligo (dT) primed cDNA library is constructed in the phage vector lambda gt11 using a poly A-selected RNA sample from human fetal skeletal muscle. Small 5'-ended clones were isolated from this library. Similarly, a human fetal skeletal muscle cDNA library can be constructed in the phage vector lambda gt10 using standard techniques as described in Koenig et al., Cell, 50:509–517 (1987).

Such a library was used to isolate six cDNA inserts detected with the above 5'-end probes. All six ended within an estimated 100 bp interval (the five longest within a 50 bp interval). This result indicates that the 5' end of the transcript is probably present in these clones. Two additional "walks" taken in the 3' direction using the most 3' segment clones from these probings also ended within 100 bp of each other, indicating that the 3' end of the transcript is probably present in these clones. As a result, the actual size of the mRNA or cDNA corresponding to the human MD gene is known to be 14 kb rather than 16 kb estimated in earlier studies described above.

Once the 5' most and 3' most ends of the human MD gene transcript are determined, the entire 14 kb cDNA is sequenced using standard techniques as described in Koenig et al., Cell, 50:509–517 (1987). The nearly complete sequence is described in FIGS. 5A–5E. The actual cDNA can be obtained from the series of cDNA probes deposited with the ATCC that in combination span the entire human MD gene. These probes are deposited under the twelve access numbers 57666 to 57677 and are depicted, in order, next to the 14 kb MD gene in FIG. 6.

These cDNA clones are tested to determine whether any clones are particularly suitable as probes of the invention. The clones are hybridized, using standard methods, to cell lines having the Xp21.3 and X;11 mutations and to mRNA from human cell lines. Suitable probes are homologous to DNA from within the Xp21.3 -X;11 region or within the mRNA. Referring to FIG. 1, suitable probes have homology to normal human cell lines but at least part of their DNA will not have homology to DNA from cell line GM7947A and the nontranslocated DNA of the cell line GM1695. A further test entails a cytological study to determine whether the clone hybridizes to the Xp21.2 chromosomal band, and thus would be suitable.

Detection of RFLPs

The probes of the invention are useful in detecting RFLPs that are closely linked with a mutated MD gene that gives rise to the DMD phenotype. Detection of such RFLPs allows diagnosis both of women who are carriers of a mutated MD gene and of unborn children who have a mutated MD gene.

EXAMPLE 5

Using pERT87 Derivatives

Using standard techniques, the subclones pERT87-8, and pERT87-15 were tested for their ability to detect human DNA RFLPs by hybridizing to nitrocellulose filters containing immobilized DNA samples from four unrelated females that had been cleaved with 24 different restriction enzymes. The frequencies of the RFLPs found in the human population were estimated by examining DNA obtained from 37 unrelated persons. The results of the search are displayed in Table 1, below. Seven potential polymorphic restriction enzyme sites were identified as individual variations in the pattern of restriction fragments observed. Two of the subclones, pERT87-1 and pERT87-8, each detected putative RFLP's of two different enzymes, while one probe, pERT87-15, detected RFLPs of three different enzymes.

TABLE 1

| 1. Subclone | Enzyme | Allele Sizes (kb) | | Allele Frequency | |
|---|---|---|---|---|---|
| | | p* | q** | p | q |
| 2. pERT87-1 | BstNI | 3.1 | 2.5/0.6 | 0.63 | 0.37 |
| 3. | XmnI | 8.7 | 7.5 | 0.66 | 0.34 |
| 4. pERT87-8 | BstXI | 4.4. | 2.2 | 0.6 | 0.4 |
| 5. | TaqI | 2.7/1.1 | 3.8 | 0.71 | 0.29 |
| 6. pERT87-15 | BamHI | 7.1/2.3 | 9.4 | 0.62 | 0.38 |
| 7. | TaqI | 3.1 | 3.3 | 0.67 | 0.33 |
| 8. | XmnI | 1.6/1.2 | 2.8 | 0.68 | 0.32 |

*common allele
**rare allele

The next step was to screen the RFLPs clones for linkage to the DMD phenotype. An RFLP is linked to the MD gene within a particular pedigree (family) if within the pedigree, persons whose DNA contains a mutant MD gene giving rise to the DMD phenotype have a polymorphic distribution different from those persons within the pedigree whose DNA does not contain a mutant MD gene. The RFLP screening was performed on pedigrees known to harbor a mutant MD gene.

The first step was to obtain DNA from a subject. In the method described below, peripheral blood lymphocytes are used; other possible sources of DNA are amniotic fluid, chorionic villus, and fetal trophoblasts.

Using standard techniques, genomic DNA is isolated from cell nuclei of whole blood leukocytes as described by Aldridge et al., Am. J. Hum. Gen., 36:546 (1984). This genomic DNA is then analyzed to determine whether linkages exist between the RFLPs of Table 1 and defective MD genes of certain families.

Figure 9:
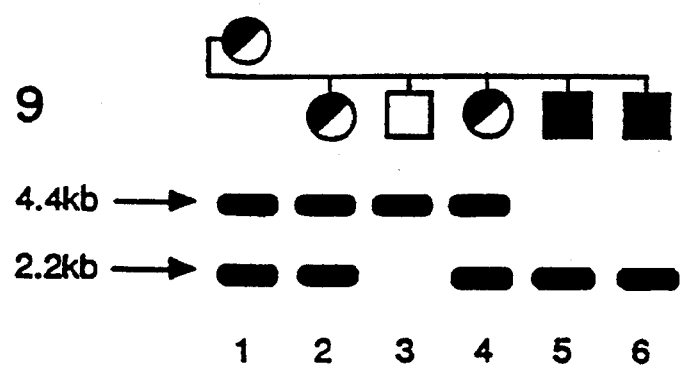
FIG. 9 is a photograph of a Southern blot analysis of genomic DNA isolated from a DMD family, probed with pERT87-8, and a schematic representation of the genotype of each family member, circles represent females, squares represent males, darkened areas indicate the presence of a MD mutant gene.

An example of such linkage is presented in FIG. 9. In the example, DNA was isolated from individuals within a family in which some people had a mutated MD gene (indicated by darkened symbols) the DNA was cleaved with BstXI, and probed with pERT87-8. Electrophoresis, blotting, and hybridization were as described above. On BstXI digestion of genomic DNA, pERT87 -8 hybridizes to 4.4 and 2.2 kb BstXI fragments in females heterozygous for the RFLP. The carrier mother exhibits the heterozygous pattern of the 4.4/2.2 kb BstXI alleles, as do her two carrier daughters (lanes 2,4). The lower allele (2.2 kb) is present in both affected DMD sons (lanes 5,6) while only the upper allele (4.4 kb) is present in the unaffected son (lane 3). The father of this family has a 4.4 kb BstXI hybridizing fragment (data not shown). The female individuals in lanes 2 and 4 were suspected of being carriers of the DMD trait based on elevated CPK values. Fragment sizes were calculated by comparison with $^{32}$P-end-labelled HindIII-cleaved λ phage DNA. Thus, the mutated MD gene is linked to the BstXI RFLP in this family, and individuals with 2.2 kb fragment also have a mutated MD gene.

Linkage between each RFLP listed in Table 1 and a defective MD gene does not occur in every pedigree. Accordingly, a combination of probes, detecting a plurality of RFLPs, is preferably used when examining DNA of an individual. Examining a combination of RFLPs listed in lines 2, 3, 5, 6, and 7 of Table 1 with the appropriate probes was found to be informative in 25 of 28 (89%) pedigrees in which members were known to have a mutated MD gene. It is also possible to use probes of the invention for presymptomatic screening of humans without a DMD phenotype for deletions (of greater than 100 bps) in the MD gene.

EXAMPLE 6

Using cDNA Probes

Although RFLP DNA marker studies are usually very useful, they are often impossible or inconclusive because family members may be unavailable, new mutation events cannot be detected reliably, meiotic crossovers within the gene occur frequently and the inheritance pattern (X-linked versus autosomal) cannot be determined with certainty in sporadic cases.

Detection of molecular deletions with the complete gene cDNA probes of the invention eliminates most of these difficulties. For example, the probes of the invention deposited with the ATCC under the access numbers 57666 to 57677, inclusive, are very useful diagnostic tools as described below.

Nuclear DNA of patients was isolated from blood leucocytes, lymphoblastoid cell lines and chorionic villi, cleaved with restriction endonucleases, transferred to Hybond (Amersham) filters, and hybridized with oligo-labelled probes, by standard techniques. cDNA segments covering the complete MD gene in a 5' to 3' direction, cloned in M13 vectors Bluescribe or Bluescript (Stratagene), are used as probes. For example, FIG. 6 shows the probes that have been deposited with the A.T.C.C. Probes 1-2a and 2b-3 comprise the most 5' 2.6 kb BglII-EcoRI fragment. Probe 4-5a is a 1.8 kb fragment and probe 5b-7 has a 2.6 kb insert. Probe 8 is a 0.9 kb EcoRI fragment. Probe 9-14 is a 6.1 kb fragment that includes the 3' exons and the 3' untranslated region.

Deletions in the MD gene do not occur in a random distribution along the cDNA, but a large percentage of the deletions can be detected with only a few probes. In a total of 104 DNA samples of unrelated DMD boys 53 exhibited a deletion of part of the MD gene. For diagnostic purposes, 27 deletions are detected with probe 8, and 15 others with probe 1-2a. These two probes detect nearly 80% of the deletions observed (42 of 53).

Particularly intriguing is the large number of deletion breakpoints found to originate within a single intron defined by probe 5b-7. One intron defined by the exons contained in this probe exhibits 19 deletion breakpoints (36% of the 53 total deletions found). Clearly this particular intron contains a characteristic that imparts a propensity for initiating deletion events. The multiple breaks could be due to a sequence-specific rearrangement hot spot, or an extraordinarily large genomic distance spanned by this intron.

The following cost-efficient strategy for the DNA-diagnostic work-up of DMD/BMD families is based on these results. Initially, DNA from affected individuals, their mothers, obligate carriers and normal male and female controls is cleaved with BglII and HindIII, electrophoresed and blotted onto nylon membranes that can be easily rehybridized. These filters are first hybridized with probe 8, exposed to X-ray film, and then rehybridized with probes 1-2a and 2b-3 in a sequential fashion. If no deletion is detected, probes 5b-7 and 4-5a are used next, and probe 9-14 is used in the final round. It is advisable to use two different restriction enzymes because fragments of similar size may co-migrate and appear as a single band on the autoradiogram. If only one of the co-migrating fragments were deleted, such a deletion could be missed. By this approach deletions should be detectable in 50% of affected males, and by careful dosage comparisons in 50% of female carriers. This direct method yields unambigous diagnoses of hemi- and heterozygosity eliminating the need for indirect linkage testing in at least half of all families. The routine analysis of families at risk for MD using the complete MD cDNA could dramatically decrease the cost and labor involved and greatly increase the accuracy of other diagnostic methods.

If no deletions are found, DNA polymorphism studies as described above are undertaken. These need to include closely linked flanking probes or segments near the 5' and the 3' ends of the gene as well as intragenic markers as argued above.

Figure 10:
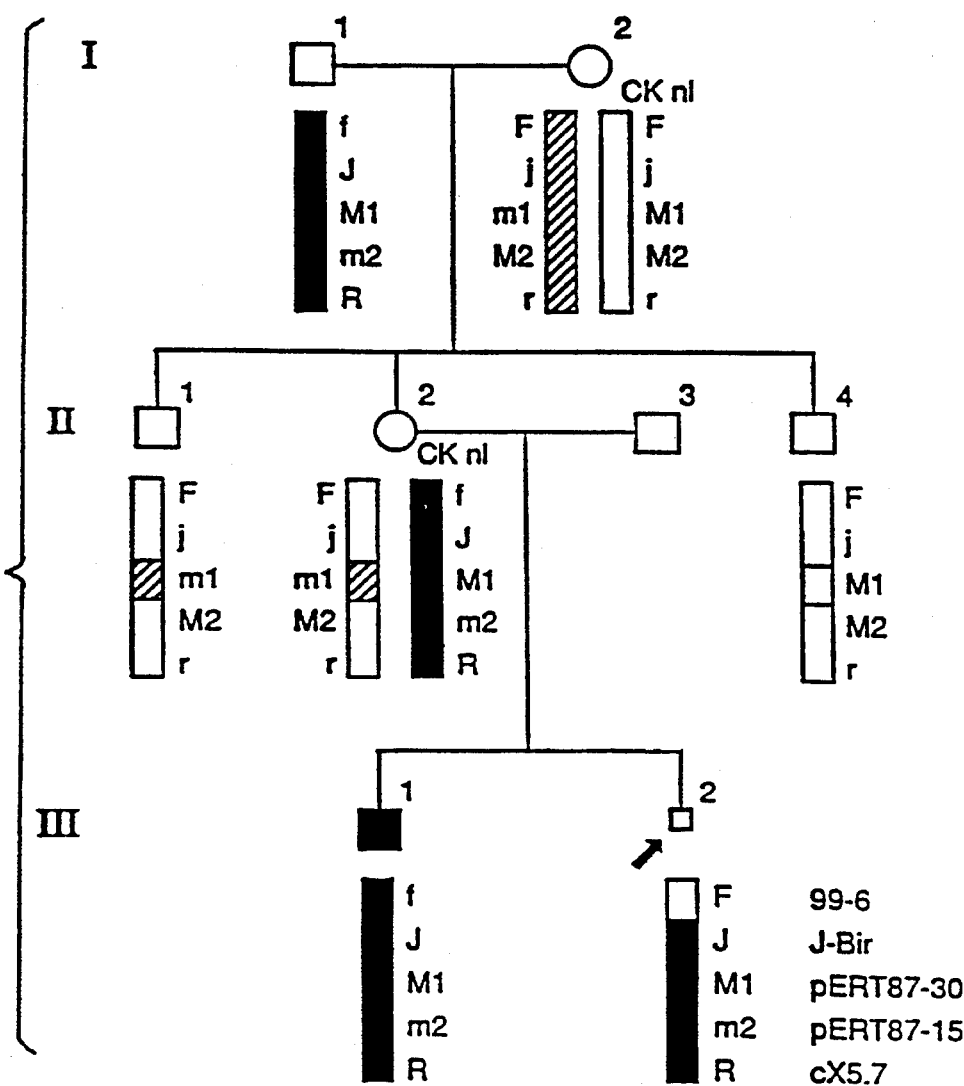
FIG. 10 is a schematic of a DNA family polymorphism study (for Family A) in which each vertical bar represents an Xp21-p22chromosome region, and each letter designates a different polymorphic DNA segment.

Following is an example of the use of cDNA probes. Family A (FIG. 10) represents a common clinical situation. That is, having only one male affected with DMD (III-1). The carrier status of his mother (II-2) was unknown, since her creatine kinase levels were in the normal range, as were her mother's (I-2). Her male fetus (III-2) was at risk. A DNA polymorphism study was carried out to determine whether the present fetus (III-2) had inherited the same X-21 region as had his affected brother. The individuals shown in FIG. 10 were tested for 21 DNA polymorphisms detected by 18 different probes, some of which are flanking the MD locus and some were subsequently shown to be derived from the gene itself. No deletions were seen with these probes. Haplotype analysis revealed that the affected male (III-1) had received his Xp21 chromosome region from his grandfather (I-1), transmitted without apparent crossover. Therefore, his grandmother (I-2) should not be a carrier, but the carrier status of his mother (II-2) remained unknown. Either she or her affected son (III-1) could represent a new mutation. Based on the DNA-marker results, the risk of the fetus (III-2) being affected was considered higher than the original 20% estimate. To prevent the abortion of a potentially unaffected fetus the usefulness of the complete gene cDNA probes of the invention was evaluated for detection of the molecular defect in the affected male.

For cDNA studies, the entire gene was surveyed for the presence of missing or abnormal-sized restriction fragments in the affected male (III-1), his mother (II-2) and controls including his unaffected maternal grandfather (I-1) from whom the Xp21 region was derived. Genomic DNA samples were cleaved with HindIII and BglII and hybridized with the cDNA probes illustrated in FIG. 6 and analyzed by known procedures. DNA extracted directly from CVS material (III-2) was digested with HindIII and BglII and analysed together with DNAs from family members (I-1, II-2, III-1), unrelated male controls (C, M1-M5) and a normal female control (F).

The mother (II-2) is apparently homozygous for all the fragments deleted in her son (III-1). The deletion detected with two adjacent segments of the cDNA likely represents the molecular basis of the DMD phenotype in the affected male. Therefore, the fetus "at risk" was determined to be unaffected with a 99% or higher probability.

Mouse MD Probes and Nucleic Acid

The above human cDNA was used as a probe in Northern blot analysis of mouse tissue mRNA. The human cDNA detected a 14 kb mouse mRNA species, which is present in very low levels in tissue extracts of mouse newborn leg and gravid (15 day) combined uterus and placenta and in higher levels in newborn heart, adult heart, and adult skeletal muscle.

In these studies, RNA was isolated from mouse tissues by homogenization of frozen, ground tissues in guanidium thiocyanate followed by pelleting through a CsCl cushion as described in Chirgwin, J. M. et al., Biochemistry 18:5294 (1979).

In order to obtain cDNAs representative of the mouse MD gene, a cDNA library was constructed from adult mouse heart as described in Gubler, U. et al., Gene 25:263 (1983) as modified in Hoffman, E. P. et al., Science 238:347–350, n.12 (1987), and screened with probes of cDNA corresponding to the human MD gene. Seven mouse cDNA clones were obtained from $5 \times 10^5$ primary (unamplified) λ gt10 recombinants, using standard techniques.

The low frequency of MD clones obtained in both human and mouse cDNA libraries suggests that the MD messenger RNA (mRNA) is rare, probably representing about 0.01 to 0.002% of the mRNA in muscle. This relative abundance is in agreement with Northern blot analyses and the frequency with which recombinant DMD clones were obtained from four other mouse and human cDNA libraries constructed in our laboratory.

Fragments of the mouse cDNA were used as probes for Southern blots of mouse genomic DNA using standard procedures as described in Hoffman et al., Science 238:347–350 (1987). In view of the 14 kb size of the complete mRNA, and assuming a constant ratio of cDNA to genomic DNA, the complete mouse MD genomic locus probably encompasses more than 500 kb of genomic DNA. Thus, the hybridization characteristics of the X-linked human MD cDNA described above are also conserved in the mouse.

The DNA sequences of the first about 4.3 kb mouse MD cDNA was determined (FIGS. 7A and 7B) and compared to human cDNA sequence. The total nucleotide sequence of 4.3 kb represents nearly 30% of the entire DMD mRNA.

Interspecies comparison of the sequences from the 5' end of the mouse and human cDNAs (FIG. 7a) show that the first 200 bp are 80% homologous with multiple insertion/deletion differences and translation stop codons in three reading frames. Furthermore, the first translation initiation codon is conserved in both humans and mice.

Both the DNA and amino acid sequences are well conserved, exhibiting 88% homology with the DNA and 87% with the amino acid sequence. There is a particularly striking conservation in the hydropathicity profile of the mouse and human amino acid sequences, the hydropathicity profiles being nearly identical. These profiles were determined according to Kyte et al., J. Mol. Biol., 157:105 (1982). Indeed, by conservative amino acid substitutions based on hydropathicity values, the mouse and human polypeptides become more than 95% homologous.

Recombinant Dystrophin and Fragments Thereof

The cDNA and predicted amino acid sequence for the 14 kb human or mouse MD gene can be used to produce recombinant dystrophin, which is named after the muscular dystrophy gene to which it corresponds. The amino acid sequence of dystrophin is shown in FIGS. 8A–8B.

For example, MD cDNA may be inserted into an appropriate vector, introduced into a cell and transcription and translation of the DNA induced, to produce dystrophin.

Similarly, smaller fragments may be produced by using only a part of the total cDNA. Myoblast cells are a suitable expression system. They are cultured and myotube formation induced by standard techniques, as described by Yasin et al., J. Neurol. Sci., 32:347–360 (1977). Other systems include bacteria, such as *E. coli*, Yeast, and cultured mammalian cells. In such systems, the dystrophin may be secreted or not and may be linked to any of several standard promoters or terminators. Dystrophin may also be produced by in vitro translation of mRNA encoding dystrophin. It may also be produced synthetically.

The above examples are not intended to limit the present invention but are merely suggestions as to how dystrophin and fragments thereof can be produced.

The invention encompasses cDNAs, mRNAs, and polypeptide sequences that are modified but substantially correspond to the cDNA and polypeptide sequences defined herein. A nucleic acid or polypeptide sequence substantially corresponds to a given sequence when it is identical except for conservative nucleotide or amino acid substitutions.

EXAMPLE 4

Dystrophin Fusion Polypeptides

The DNA and predicted amino acid sequences for 4.3 kb (30%) of the mMD gene described above were used to produce fusion polypeptides and substantially purified mouse dystrophin.

Two different regions of the mouse heart mMD cDNA were fused to the 3' terminus of the *E. coli* trpE gene using the expression vector pATH2 (Dieckmann et al., J. Biol. Chem 260:1513–1520 (1985)). The two regions represent the majority of the mouse heart cDNA sequence described above and shown in FIG. 7B. One construction resulted in the fusion of approximately 30 kD of mMD dystrophin to the 33 kD trpE polypeptide, while the second fused roughly 60 kD of the mMD polypeptide. Since the trpE polypeptide is insoluble, quantitative yields of induced fusion polypeptides were obtained by lysing the cells and precipitating insoluble polypeptides. Novel insoluble fusion polypeptides of the expected size were produced which were not present in lysates of bacteria containing the pATH2 vector alone.

To produce the trpE+60 kD fusion, the mouse MD cDNA was restricted at the unique SpeI site, blunt-ended with Klenow, and then digested with HindIII in the 3' polylinker. The excised cDNA fragment of 1.4 kb was gel purified and ligated to pATH2 which had been digested with SmaI and HindIII. Recombinants were identified by colony hybridization and verified by subsequent plasmid DNA restriction analysis. The resulting plasmid construction fused the trpE polypeptide (33 kd) to 410 amino acids (~60 kD) of the mMD polypeptide, and corresponds to position 1.3 kb to 2.7 kb on the equivalent human cDNA map.

To produce the trpE+30 kD fusion, the most 3' end of the mouse cDNA was restricted at its unique non-methylated XbaI site, and at the BamHI site in the 3' polylinker. The excised 700 bp fragment was ligated to pATH2 and digested with XbaI and BamHI as described above. This plasmid construction fused the trpE polypeptide to 208 amino acids (~30 kD) of the mDMD polypeptide, and corresponds to position 3.7 kb to 4.4 kb on the equivalent human cDNA map.

Antibodies to Dystrophin or Fragments Thereof

Antibodies can be raised by standard techniques to any of the above described recombinant dystrophin, or fragments thereof. Further naturally ocurring dystrophin may also be used. The following is an example of such a method and is not limiting to this invention.

Both of the fusion polypeptides described above were purified by preparative SDS-polyacrylamide gel electrophoresis (Laemmli, Nature 227:680–685 (1970)), and used to immunize rabbits and sheep. Rabbits were immunized with electroeluted, 'native' (free from SDS) insoluble antigen, while sheep were immunized with SDS-polyacrylamide gel slices containing denatured antigen.

The titers and specificity of the antibodies produced in each rabbit were constantly monitored by enzyme-linked immuno-assays performed on nitrocellulose dot blots of insoluble polypeptide fractions. The best immune responses were obtained using the trpE+30 kD polypeptide with >95% of the antibodies produced being specifically against the mDMD portion of the fusion peptide, and with titers greater than the sensitivity of the ELISA assay system when using a 1:1000 dilution of crude serum 4 weeks after immunization. The trpE+60 kD antigen took much longer (12 weeks) to evoke a immune response in rabbits, with the resulting sera showing a low specificity for the MD portion of the fusion polypeptide.

To ensure that any polypeptide species identified by the antisera was due to recognition by antibodies specific for the MD portion of the fusion polypeptides, rabbit and sheep antibodies directed against the 30 kD antigen, and sheep antibodies directed against the 60 kD antigen were affinity purified. Affinity purification (AP) of the antibodies directed against the MD portion of the fusion polypeptide is facilitated by the insolubility of the partially purified fusion polypeptide. In general, by simply resuspending crude insoluble trpE polypeptide fractions in immune serum, antibodies against the trpE polypeptide are eliminated. Antibodies specific for the MD polypeptide are then isolated by binding with fusion polypeptides. These antibodies allow detection of as little as 1 ng of dystrophin in 50 μg muscle tissue.

For example, approximately 3 mg of a partially purified insoluble fraction of trpE polypeptide is precipitated, resuspended in 10 mM Tris (pH 8.0), and then precipitated again. The pellet is resuspended in 1.5 ml of immune serum, incubated on ice for 1 hour, then centrifuged to pellet the trpE-antibody immune complexes, which are discarded. The supernatant is then mixed with approximately 3 mg of partially purified fusion polypeptide (insoluble fraction) which has been washed as above. After incubation on ice, the mDMD-antibody immune complexes are precipitated by centrifugation. The pellet is then resuspended in 500 ul of 0.2M glycine (pH 2.3), incubated on ice for 5 minutes to disassociate the immune complexes, and then centrifuged at 4° C. to precipitate the insoluble antigen. The supernatant contains purified anti-MD immunoglobulins and is neutralized with 50 ul Tris (pH 9.5), and either stabilized with BSA (fraction V) 5 mg/ml) or dialyzed extensively against phosphate buffered saline (PBS).

The invention also contemplates the production of monoclonal antibodies to dystrophin or fragments thereof. Such monoclonal antibodies are secreted by hybridomas produced by standard techniques.

Natural Dystrophin

Naturally occuring dystrophin can be identified using the above-described antibodies. For example, total polypeptide samples were isolated from mouse (fresh) and human (frozen) tissues by direct solubilization of tissues in ten volumes of gel loading buffer (100 mM Tris pH 8.0, 10% SDS, 19 mM EDTA, 50 mM DTT). Alternatively, Triton X-100 insoluble fractions are isolated from human and mouse tissues by homogenizaton in 0.25% Triton X-100 using a Waring blender at full speed, and pelleting insoluble polypeptides. All polypeptide samples (50 ug) are separated by electrophoresis on 3.5% to 12.5% gradient SDS-polyacrylamide gels (Laemmli, Nature 227:680–685 (1970)) using a 3.0% stacking gel, and transferred to nitrocellulose (Towbin, Proc. Nat. Acad. Sci. USA 76:4350–4354 (1979)). Identical nitrocellulose blots of the separated polypeptides are incubated with affinity purified rabbit antibodies directed against the 30 kD antigen, affinity purified sheep antibodies directed against the 60 kD antigen, and affinity purified sheep antibodies directed against the 30 kD antigen each at a 1:1000 dilution. Immune complexes are detected using either $^{125}$I-polypeptide A, or alkaline phosphatase conjugated donkey anti-sheep IgG second antibody (sheep IgG binds very poorly to polypeptide A). All antibodies detect a large molecular weight, apparently low abundance polypeptide species calculated to be approximately 400 kD in total. The higher resolution of the alkaline phosphatase staining resolves this polypeptide into doublets or triplets, though the slightly smaller bands most likely represent degradation products since there has been no evidence to date for alternatively spliced isoforms of the MD mRNA. The 400 kD species is clearly evident in mouse smooth muscle (stomach), though at a level that is substantially less than that found in cardiac and skeletal muscle. The same apparent polypeptide species is detectable in mouse brain at an extremely low level.

The 400 kD polypeptide species recognized by the antibodies of the invention is generally Triton-insoluble, though it appears to be associated more strongly with the myofibrillar matrix fraction in cardiac muscle than in either skeletal muscle or smooth muscle. The 400 kD polypeptide species is present in the skeletal and cardiac muscle of both normal and Tr mice. The detected polypeptide appears the same with a mixture of antisera as it does with each antiserum seperately, indicating that the antibodies raised against different antigens recognized the same polypeptide. Both antibodies fail to detect the 400 kd polypeptide in muscle tissues isolated from mice harboring either allele of the mdx mutation.

Immunodiagnosis

The antibodies described above can be used in a variety of immunological applications to test for the presence of dystrophin or fragments thereof in biological samples. For example, the antibodies can be labelled by conventional procedures with $^{125}$I, $^{35}$S, or $^{3}$H for use in radioimunoassays, with fluorescein for fluorescent assays, with enzyme for enzyme immunoassays, or with biotin for biotin-avidin linked assays.

These antibodies can be used labelled or unlabelled as desired and can be employed in competitive immunoassays as well as in double antibody or "sandwich" assays. Monoclonal antibodies can also be used in standard techniques to test polypeptides for cross-reactivity with dystrophin.

The antibodies can also be immobilized on an insoluble phase, such as an insoluble resin. The dystrophin level is then detected by measuring the amount of binding to the insoluble phase. Other insoluble phases include latex particles, which will agglutinate when coated with the novel antibodies and subjected to certain levels of dystrophin in the sample. Yet other insoluble phases include test tubes, vials, titration wells, and the like to which the antibodies according to the invention can be bound and the dystrophin "antigen" thereto detected by double antibody techniques or Protein A dependent techniques. These antibodies are also useful for purification of dystrophin by affinity purification as described above.

In particular, the antibodies according to the invention can be used for the immunodiagnosis of MD. Futhermore, these novel antibodies can be used to distinguish between Becker's MD (BMD), Duchenne's MD (DMD), Outlier's MD (OMD) and other neuromuscular disorders. For example, muscle biopsies of patients can be prepared and tested according to the invention to determine with a high degree of accuracy whether the patient has DMD, BMD, OMD, or no MD.

To perform such a test, small portions of the biopsies (less than 0.1 g) are crushed into a very thin sheet of tissue using a pestle and a plastic weigh boat on a hard surface at −20° C. The tissue fragments are then weighed at 4° C., and immediately placed in 20 volumes of loading buffer (10% SDS, 50 mM DTT, 10 mM EDTA, 0.1M Tris pH 8.0, 0.001% bromophenol blue) and vigorously shaken. Samples are stored at 4° C. prior to use.

Samples are placed in a boiling water bath for two minutes, then centrifuged to remove SDS-insoluble polypeptides. Supernatants (1–2 ul; 50 ug) are loaded on 20 well, 0.8 mm×15 cm×17 cm SDS-polyacrylamide gels (Laemmli, Nature, 227:680–85 (1970)), using a 3% (0.1% bisacrylamide) stacking gel and 3.5%–12.5% gradient resolving gel. Fractionated polypeptides are transferred to nitrocellulose (Towbin, H. et al., PNAS, 76:'4350–54 (1979)), then incubated with the affinity purified sheep anti-mouse dystrophin described above. Dystrophin/antidystrophin immune complexes are detected using affinity purified donkey anti-sheep IgG second antibody conjugated to alkaline phosphatase (Sigma), followed by colorimetric development. All gels are stained with Coomassie Blue after transfer to determine the efficiency of the transfer.

Residual myosin in the post-transfer Coomassie blue-stained gels serves as a control for the amount of muscle tissue contained in the biopsy. The accuracy of this residual myosin quantitation of muscle polypeptide is verified by alpha-actin immunostaining after dystrophin staining is completed, or by calsequestrin immunostaining.

EXAMPLE 7

Muscle Immunodiagnosis

Samples from 103 muscle biopsies were analyzed. All samples were scored for the abundance and apparent size of the polypeptide product of the MD gene, dystrophin, described above.

Figure 11A:
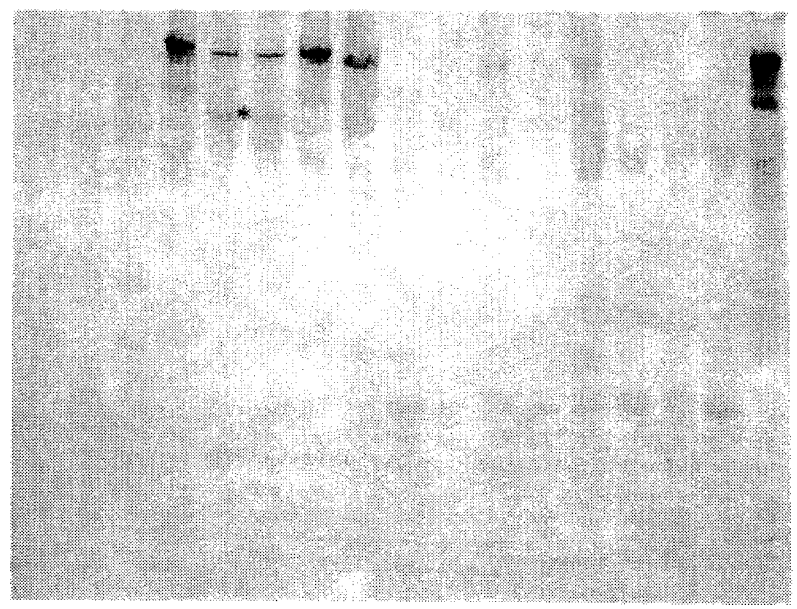
FIGS. 11A and 11B are photographs of immunostained Western blot gels containing muscle samples of DMD, BMD and OMD patients.
Figure 11B:
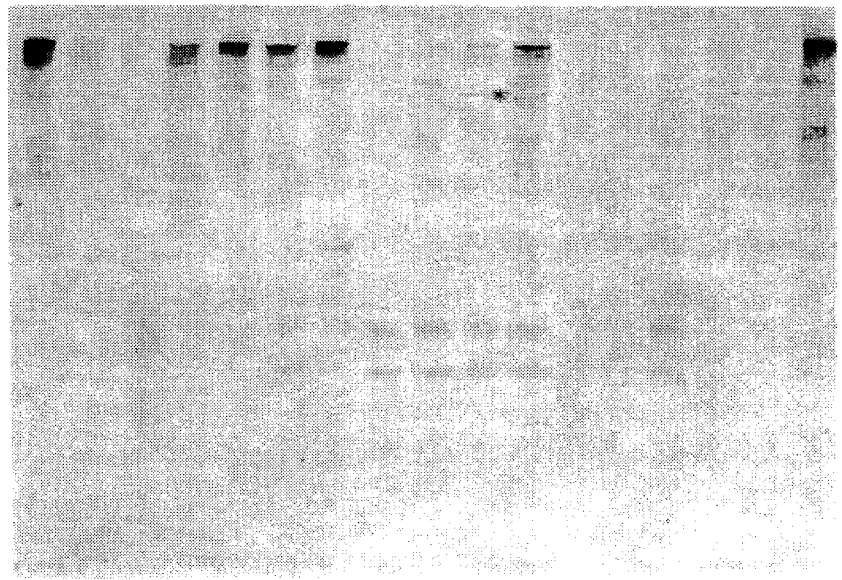

The abundance and apparent molecular weight of dystrophin contained in 103 muscle biopsies from various neuromuscular disease patients was determined relative to a normal control (examples are shown in FIG. 11). Biopsies obtained from patients previously diagnosed as Duchenne exhibited dramatically reduced levels of dystrophin (FIG. 11a, lanes 1, 2, 9–16; FIG. 11b, lanes 3, 8, 9, 12, 14, 16) relative to the normal control (FIG. 11a, lane 17; FIG. 11b, lanes 1, 5, 17). On the other hand, most patients previously diagnosed as being afflicted with a neuromuscular disorder unrelated to Duchenne or Becker exhibited dystrophin levels indistinguishable from the normal control (FIG. 11b, lanes 6, 7). The Becker biopsy samples exhibited a more variable dystrophin phenotype (FIG. 11a, lanes 3, 5, 6; FIG. 11b, lanes 2, 4, 10, 11). Some Becker biopsies contained dystrophin of apparently smaller molecular weight but of nearly normal abundance (FIG. 11a, lanes 5, 6). One Becker shown in FIG. 11b, lane 2, appeared to have dystrophin which was larger in size, but reduced in abundance to approximately 40% of normal. Another Becker exhibited a dystrophin phenotype which was undistinguishable from normal (FIG. 11b, lane 4), while an additional Becker contained no detectable dystrophin in his biopsy (FIG. 11a, lane 3). Three 'Outlier' biopsies (mild Duchenne/severe Becker) are also shown, two of which exhibit dystrophin of low abundance (FIG. 11a, lane 11; FIG. 11b, lane 15), while the third contains no detectable dystrophin (FIG. 11b, lane 13).

majority of Duchenne patients exhibit undetectable levels of dystrophin, the Outliers (mild Duchenne/severe Beckers; included two affected females) exhibit low levels of dystrophin of normal size, while most Beckers exhibit nearly normal levels of dystrophin of abnormal size.

There are individual patients whose clinical phenotype clearly does not correlate with the dystrophin phenotype (Table 2, asterisks). These patients comprised 7.7% of the total patients studied (8/103).

TABLE 2

Results of dystrophin analysis in 103 patient biopsies.

| Dystrophin Data | Clinical Diagnoses | | | |
|---|---|---|---|---|
| | Duchenne | Outliers | Becker | Non-DMD/BMD |
| I. Normal size, 60–100% level | 1 (2.6%)* | | 4 (22.2%)* | 38 (95.0%) |
| II. Abnormal size, 40–100% level | | 1 (14.3%) | 12 (66.6%) | 2 (5.0%)* |
| III. Normal size, 3–60% level | 1 (2.6%) | 4 (57.1%) | 1 (5.5%) | |
| IV. Abnormal size, 3–40% level | 1 (2.6%) | 1 (14.3%) | | |
| V. <3% level or undetectable | 35 (92.1%) | 1 (14.3%) | 1 (5.5%)* | |
| Totals | 38 | 7 | 18 | 40 |

Figure 12:
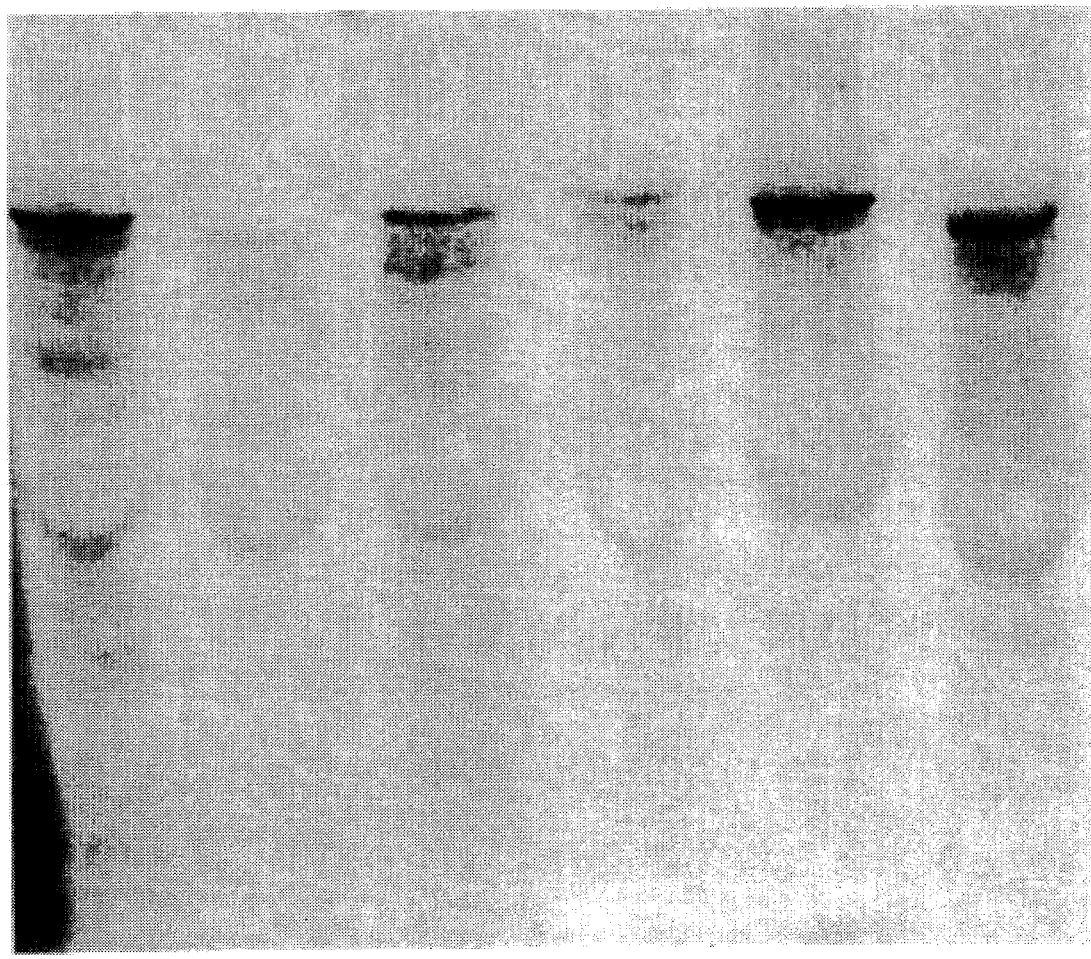
FIG. 12 is a photograph of an immunostained Western blot containing muscle samples of BMD patients and normal non-MD controls.
Figure 13A:
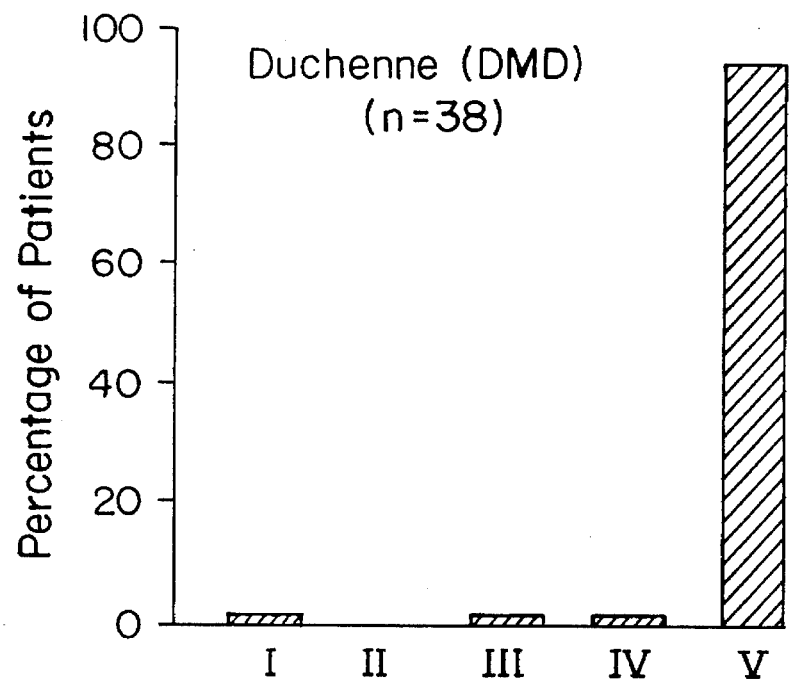
FIGS. 13A–13D are a set of charts depicting the distribution of dystrophin biochemical phenotypes.
Figure 13B:
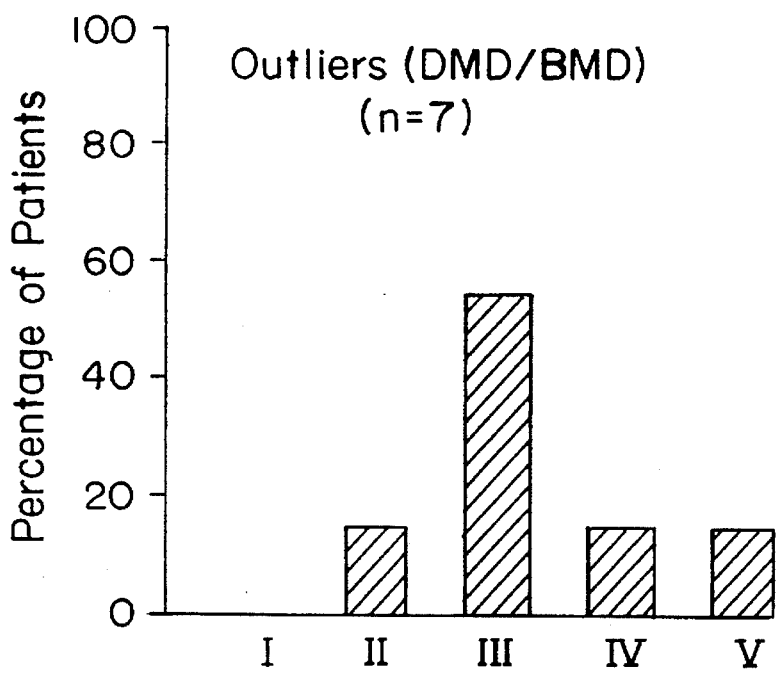
Figure 13C:
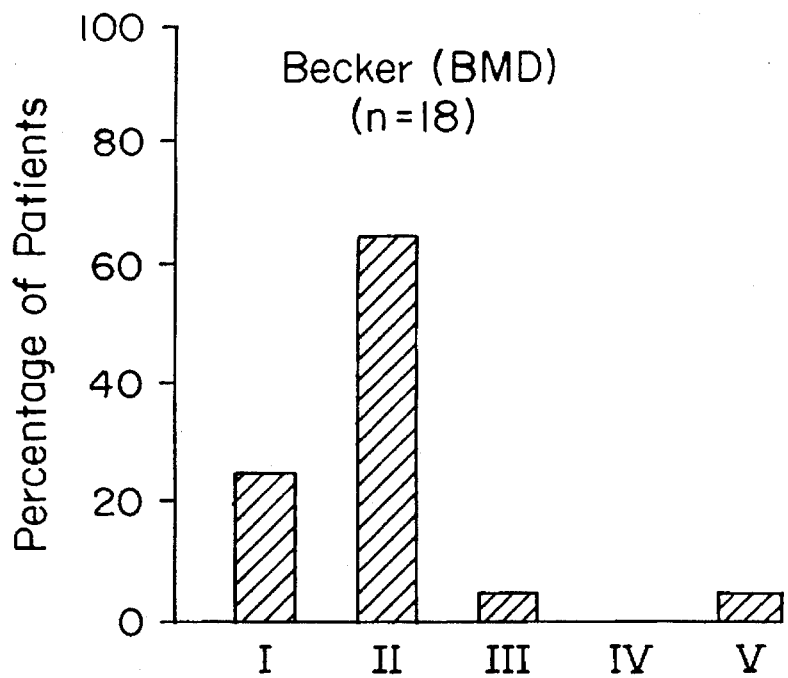
Figure 13D:
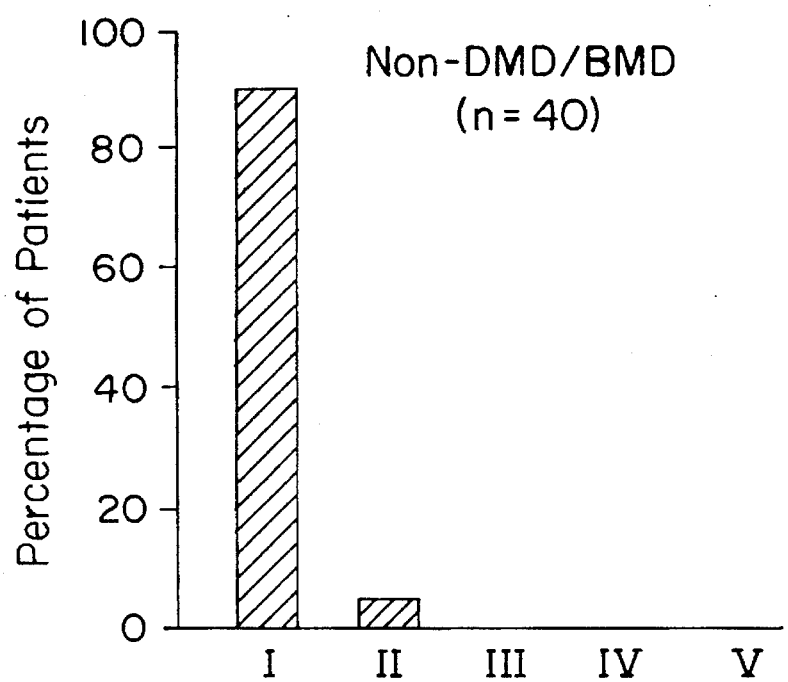

The size variations of dystrophin were often subtle, such that it was difficult to unambiguously determine size differences if the sample in question was not run immediately adjacent to normal controls (see two Becker biopsies, FIG. 11b, lanes 10, 11). For this reason, all samples containing detectable dystrophin determined by the above analysis were retested adjacent to normal controls. An example of this analysis is shown in FIG. 12. The three Becker biopsies shown contain dystrophin which was either clearly smaller (lanes 2, 6) or larger (lane 4) than that of the normal controls (lanes 1, 3, 5).

The described experimental process was reported for each of the 103 biopsies included in the study. The dystrophin molecular weight (normal vs. abnormal size), and abundance relative to the normal control sample was thus calculated for each patient's biopsy. Five dystrophin 'phenotypes' were established which accounted for all patient dystrophin data, and which seemed to correlate to disease type and severity. These dystrophin phenotypes ranged from 'normal' (normal size, 60–100% of normal abundance), to 'severe' (less than 3% of normal abundance). The number and percentage of patients under each of four clinical categories (Duchenne, Outliers, Becker, non-DMD/BMD) was then tabulated with regards to the five dystrophin phenotypic classes (Table 2).

Ninety-five percent (38/40) of the patients previously diagnosed as having disorders unrelated to Duchenne or Becker muscular dystrophy exhibited completely normal dystrophin phenotypes. On the other hand, 92% (58/63) of the patients previously diagnosed as having a Duchenne/Becker dystrophy exhibited a clearly abnormal dystrophin phenotype. Within the Duchenne/Becker individuals exhibiting an abnormal dystrophin phenotype there was a clear correlation between the severity of the clinical phenotype and the 'severity' of the dystrophin phenotype (FIGS. 13A–13D, roman numerals correspond to categories in Table 2). From this analysis it becomes apparent that the Therapy The dystrophin or biologically functional fragments thereof can also be used in a method of therapy for MD. A biologically functional polypeptide fragment is capable of causing the same biological effects as the normal full polypeptide. The method of therapy involves administering an amount of the dystrophin or biologically functional fragments thereof effective to control muscle fiber degeneration and connective tissue proliferation within muscle fibers.

The dystrophin and related polypeptides as described above can be administered by routine methods. For example, they can be injected directly into the blood stream or muscle of an animal or human patient to a final concentration of between 1 and 500 mg/ml of serum, most preferably 200 mg/ml. This dose is repeated to maintain this level.

A further method of therapy involves removing cells, such as muscle cells, from an MD patient and incorporating MD DNA into them. The 14 kb cDNA of the invention, or a fragment thereof, is linked to a suitable promoter and inserted into a suitable vector. The vector is then introduced into the cells harvested from the patient and the genetically manipulated cells induced to produce the dystrophin polypeptide, or biologically functional fragments thereof. These cells are then reintroduced into the patient, for example, intravascularly or intramuscularly.

Deposit

Figures 6A, 6B:
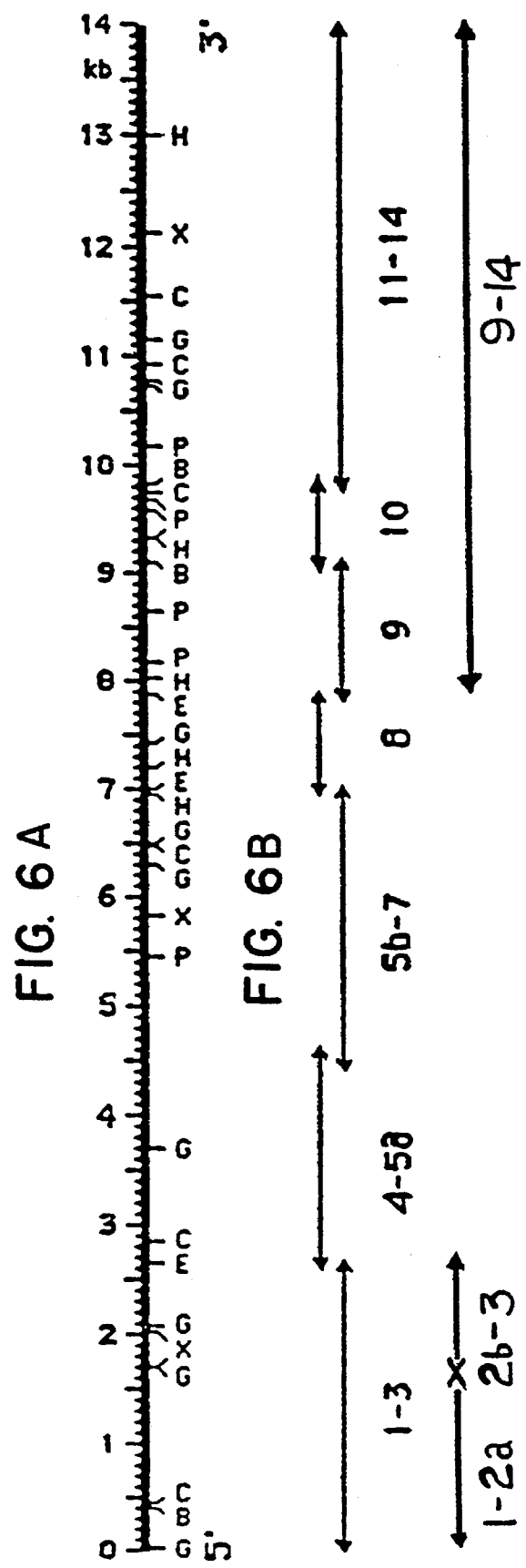
FIG. 6A is a restriction map of the 14 kb cDNA encoding the MD gene.
FIG. 6B is a diagrammatic representation of cDNA fragments that in combination span the entire 14 kb cDNA.

The complete 14 kb cDNA sequence depicted in FIG. 5 has been deposited in the form of 6 cDNA probes depicted in FIG. 6a. These 6 probes have been deposited with the ATCC under the access numbers 57666 to 57677, inclusive. The deposit was made on Jul. 15, 1987. Each probe is deposited as a purified plasmid and as a plasmid in E. coli. Hence, each probe has two access numbers.

Applicants' assignee, Children's Medical Center Corporation, acknowledges its responsibility to replace these cultures should they die before the end of the term of a patent issued hereon, 5 years after the last request for a culture, or 30 years, whichever is the longer, and its responsibility to notify the depository of the issuance of such a patent, at which time the deposits will be made irrevocably available to the public. Until that time the deposits will be made available to the Commissioner of Patents under the terms of 37 CFR Section 1.14 and 35 Section 112.

Other embodiments are within the following claims.

We claim:

1. An isolated antibody that specifically binds to dystrophin.

2. The antibody of claim 1 wherein said antibody is a monoclonal antibody.

3. The antibody of claim 1 wherein said antibody specifically binds to human dystrophin.

4. A method for detecting the presence of dystrophin in a human, comprising the steps of
   (a) obtaining a muscle cell or muscle tissue sample from the human;
   (b) separating dystrophin in said sample from other proteins by SDS-polyacrylamide gel electrophoresis;
   (c) contacting the dystrophin with the antibody of claim 3, thereby producing an antibody-dystrophin complex;
   (d) visualizing the antibody-dystrophin complex; and,
   (e) determining the molecular weight of said complex, wherein the presence of said complex having a molecular weight of about 400 kD is indicative of the presence of dystrophin.

5. A method for diagnosing muscular dystrophy in a human, comprising the steps of
   (a) obtaining a muscle cell or muscle tissue sample from the human;
   (b) separating dystrophin or fragments of dystrophin in said sample from other proteins by SDS-polyacrylamide gel electrophoresis;
   (c) contacting the dystrophin or fragments of dystrophin with the antibody of claim 3, thereby producing an antibody-dystrophin complex or an antibody-dystrophin fragment complex;
   (d) visualizing the antibody-dystrophin complex or antibody-dystrophin fragment complex; and,
   (e) determining the molecular weight of said antibody-dystrophin complex or said antibody-dystrophin fragment complex, wherein the absence of said antibody-dystrophin complex having a molecular weight of about 400 kD is indicative of muscular dystrophy.

6. The method of claim 5 wherein the presence of said antibody-dystrophin complex having a molecular weight other than about 400 kD, or said antibody-dystrophin fragment complex having a molecular weight other than about 400 kD, is indicative of muscular dystrophy.

7. A method for diagnosing muscular dystrophy in a human, comprising the steps of
   (a) obtaining a muscle cell or muscle tissue sample from the human;
   (b) separating dystrophin or fragments of dystrophin in said sample from other proteins by SDS-polyacrylamide gel electrophoresis;
   (c) contacting the dystrophin or fragments of dystrophin with the antibody of claim 3, thereby producing an antibody-dystrophin complex or an antibody-dystrophin fragment complex;
   (d) visualizing the antibody-dystrophin complex or antibody-dystrophin fragment complex; and,
   (e) determining the molecular weight of said antibody-dystrophin complex or said antibody-dystrophin fragment complex, wherein the presence of a reduced amount of said antibody-dystrophin complex having a molecular weight of about 400 kD, as compared to amounts of said complex present in a normal human muscle cell or tissue sample, is indicative of muscular dystrophy.

8. The method of any one of claims 4, 5, 6, or 7, wherein said sample is obtained from a human child.

9. The method of any one of claims 4, 5, 6, or 7, wherein said sample is obtained from a human adult.

* * * * *